United States Patent [19]

Consadori et al.

[11] Patent Number: 5,526,280
[45] Date of Patent: Jun. 11, 1996

[54] METHOD AND SYSTEM FOR GAS DETECTION

[75] Inventors: Franco Consadori, Salt Lake City; D. George Field, Pleasant Grove; Kevin D. Banta, Sandy, all of Utah

[73] Assignee: Atwood Industries, Inc., Rockford, Ill.

[21] Appl. No.: 234,013

[22] Filed: Apr. 28, 1994

[51] Int. Cl.⁶ .................. G01N 27/16; G06F 17/00
[52] U.S. Cl. .................. 364/496; 364/497; 340/632; 340/633; 73/23.2; 73/23.31; 73/25.01; 73/31.05; 422/94; 422/95; 422/98; 436/151
[58] Field of Search .................. 364/496, 497, 364/498, 499; 340/632, 633, 634; 73/23.2, 23.31, 25.01, 31.05; 422/83, 94, 95, 98; 436/137, 151; 338/34

[56] References Cited

U.S. PATENT DOCUMENTS

| | | | |
|---|---|---|---|
| 4,340,885 | 7/1982 | Chavis et al. | 340/632 |
| 4,384,283 | 5/1983 | Drope et al. | 340/632 |
| 4,390,869 | 6/1983 | Christen et al. | 340/632 |
| 4,542,640 | 9/1985 | Clifford | 73/23 |
| 4,630,038 | 12/1986 | Jordan | 340/632 |
| 4,644,333 | 2/1987 | Barendsz et al. | 340/634 |
| 4,663,958 | 5/1987 | Matthiessen | 73/1 G |
| 4,670,405 | 6/1987 | Stetter et al. | 436/151 |
| 4,705,617 | 11/1987 | Beebe et al. | 364/497 |
| 4,720,993 | 1/1988 | Badwal | 73/23 |
| 4,761,639 | 8/1988 | Pyke et al. | 73/23.2 |
| 4,847,783 | 7/1989 | Grace et al. | 364/497 |
| 4,854,155 | 8/1989 | Poli | 73/31.05 |
| 4,860,223 | 8/1989 | Grilk | 364/496 |
| 4,881,183 | 11/1989 | Groe | 364/497 |
| 4,887,455 | 12/1989 | Payne et al. | 73/27 |
| 4,896,143 | 1/1990 | Dolnick et al. | 340/634 |
| 4,911,892 | 3/1990 | Grace et al. | 422/94 |
| 4,943,929 | 7/1990 | Simonoff | 364/496 |
| 5,034,725 | 7/1991 | Sorensen | 340/632 |
| 5,055,269 | 10/1991 | Palumbo et al. | 73/23.31 |
| 5,061,447 | 10/1991 | Ono | 73/31.05 |
| 5,066,466 | 11/1991 | Hölter et al. | 340/632 |
| 5,142,898 | 9/1992 | Kauschke et al. | 73/23.31 |
| 5,184,500 | 2/1993 | Krema et al. | 364/498 |
| 5,276,434 | 1/1994 | Brooks et al. | 340/632 |
| 5,331,310 | 7/1994 | Stetter et al. | 340/632 |
| 5,356,819 | 10/1994 | Ritschel | 73/25.01 |

*Primary Examiner*—Ellis B. Ramirez
*Assistant Examiner*—Eric W. Stamber
*Attorney, Agent, or Firm*—Workman, Nydegger & Seeley

[57] ABSTRACT

A system and method for using a gas detecting device that conducts electricity increasingly for increasing concentration of a gas being detected. The temperature of a gas sensor element is regulated to first burn-off impurities on the surface thereof, and then to cool down the gas sensor element to a temperature at or above which the gas catalyzes. During catalyzation, the sensor element conducts and electrically signals a microprocessor concentration data, which microprocessor controls a three color LED so as to emit a color pattern indicative of the concentration level of the gas. A sum of previously measured concentration levels is taken to gauge exposure to the gas over a period of time. The gas detection system includes a self-calibration routine that can be run prior to normal use by successive exposure to varying concentrations of gas to determine the sensor element-specific reaction. The sensor element output at each known concentration level is stored in nonvolatile memory during the self-calibration routine, which stored calibration data is compared to values measured during normal operation to accurately detect gas concentration levels. Audible alarms sound when the sum of previously measured concentration levels exceeds a predetermined hazardous level.

33 Claims, 22 Drawing Sheets

METHOD AND SYSTEM FOR GAS DETECTION

BACKGROUND

1. Field of the Invention

This invention is related to gas detection and monitoring, and more particularly to a system and method which utilize an electronically monitored gas sensor system to automatically detect, measure concentration, and announce the presence of toxic gaseous substances.

2. Background Art

Gas sensors haven been known and used in systems to detect the presence of toxic gases for a number of years in connection with a wide variety of applications, including residential and recreational vehicle use. Detectors are desirable in such uses due to the fuel combustion bi-products that enter the occupancy spaces thereof. A gasoline burning engine, a residential gas water heater, or furnace are examples of combustion that produce toxic gases.

A typical toxic by-product of fuel combustion is carbon monoxide gas (CO). When fuel that contains carbon is combusted, there will be a generation of carbon monoxide. The presence of CO in combustion is often accompanied by odors characteristic of the combustion process which may be pleasant, such as incense, resin in burning logs, or tobacco products. However, CO is odorless and tasteless. Additionally, CO is highly reactive, burns easily, is explosive, and is lethal to human beings. For good reasons, the detection of CO in high concentration levels is desirable to meet safety concerns.

In order to properly protect human beings from CO, a gas detection system must be capable of performing several functions. First, it must be able to detect carbon monoxide. Second, it must be able to deal with the information gathered by the gas detection system in a way that effectively balances the need to alarm or warn as to the presence of dangerous levels of CO, while also preventing false warnings and alarms. A gas detection system giving false alarms tends to lower the dependance and reliance of those being warned. To minimize these false alarm events, a detector must be provided that is effective to detect and warn as to truly hazardous conditions. Otherwise, those who are being falsely alarmed will eventually ignore its alarms or will disconnect the detector because of an unwillingness to tolerate the confusion of false alarms. For example, if a detect 6r gave a long and loud audible alarm whenever a toaster toasted bread or a fire was made in a fire place, the tolerance for such noise may be limited.

To be effective, a gas detection system must be capable of detecting CO in the concentration range and duration thereof which are of interest to human safety, while filtering out brief periods of relatively high gas concentration levels which may be of no consequence. Typically, an effective gas detection system must be able to detect at least 50 parts per million CO in the air. To avoid false alarms as to transient or momentary high levels of CO, the effective gas detection system must also determine a length or time of exposure to a hazardous CO level. Thus, a gas detector system that detects both the concentration of CO and the duration of exposure to hazardous concentrations of CO will accumulate a proper amount of information in order to warn those being exposed, rather than to set off an alarm each time any high level of CO concentration is detected.

High levels of CO are not necessarily dangerous when the exposure period is transient or momentary. For instance, it is not immediately harmful for a human being to breathe a large concentration of carbon monoxide such as 1,000 ppm for one or two breaths. Thus, a gas detector system that sets off an alarm when such a brief concentration is present in the air, even if it is present only for 10 seconds, is a gas detection system that is less effective psychologically to the user thereof.

High concentration exposures to CO are typical in every day events, such as taking a couple of breaths while walking behind a car that is not properly tuned. Improperly tuned automobiles produce a large amount of CO. Another example of possibly high CO generation is lighting a fire in a fireplace or lighting a charcoal grill. Determining a harmful exposure to CO involves both concentration level and the length of time there will be an exposure thereto.

In the past, others have made efforts to detect CO in the air with gas detection systems which put out an alarm for a concentration of both high concentration level and duration. Highly accurate systems prove to be expensive and impractical, such as laboratory gas analysis equipment. It would be desirable to provide an effective gas detection system that costs a fraction of the cost of laboratory gas detection equipment.

Semiconductor devices which are capable of detecting CO are becoming less expensive. Such semiconductors have a sensor element that is heated by a heater element to a predetermined temperature. The predetermined temperature is temperature at and above which the gas that is to be detected will catalyze. Different gases catalyze at different temperatures when in fluid contact with the sensor element that has been heated by the heater element to a gas-specific temperature. When the sensor element is heated to the gas-specific temperature, the gas will catalyze in a reaction with the exposed surface areas of the sensor element causing it to conduct electricity somewhat proportionally, but non-linearly, to the concentration level of the gas. Electrically, the resistivity or the resistance of the sensor element gets lower as the concentration gets higher. The current through the sensor element gets higher as the concentration level gets higher. Stated otherwise, resistivity of the sensor element increases as the concentration level decreases in an inversely proportional but non-linear relationship.

While CO detecting semiconductors have a long operational life, they also may yield false alarms due to the presence of extraneous gases, due to humidity, or due to uncompensated sensitivity of a sensor element to ambient temperature which causes the signal produced therefrom to be skewed.

In order to measure concentration levels of a particular gas, such as CO, the sensor element should be heated to the gas-specific temperature. As the sensor element cools down in a cyclic excitation, impurities also adhere to the surface of the sensor element. When kept at a constant high temperature, the impurities do not tend to build up because they will catalyze by adsorption. Thus, it is advantageous to heat the sensor element to an elevated temperature, above the predetermined gas-specific temperature for measuring gas concentration levels, in order to catalyze the impurities off of the sensor element.

Electrical power is modulated as it is applied to the sensor heater element so as to heat up and cool down the sensor element to cyclically measure gas concentration levels and catalyze off impurities. To measure the concentration level of the gas desired to be detected, an electrical potential is applied to the sensor element while it is heated to the gas-specific temperature and then the change in current is measured which corresponds to the concentration level of the gas. The greater the thermal mass of the sensor element being cyclically heated and cooled, the longer the heat-up and cool-down cycle, the longer the time between gas concentration readings, and the more power consumption needed to raise the temperature of the sensor element while accurately measuring gas concentration by catalyzing impurities. By increasing the number of such reading and catalyzing cycles over a period of time, a more accurate assessment of the dynamic nature of toxic gas concentration levels can be made. Thus, it would be an improvement in the art to maximize power efficiency by minimizing the thermal mass of the sensor element, minimizing the heat-up and cool-down cycle time, and maximizing the number of readings of gas concentration levels over a period of time.

Gas detectors systems whose purpose is to protect against human hazards have their goal to keep the level of CO that is inhaled by human to a safe amount. Inhaled CO becomes COHb in the blood of an inhaling human. COHb in the blood is a function of both CO concentration and inhaling over time. Mathematical algorithms to calculate COHb can be analytical, complex analytical, or numerical. Each of such algorithms, when used in real time gas detection systems, involve varying amounts of data, processing speed and power. It is desirable to keep processor costs down and speeds up by using algorithms that give good numerical approximates of COHb with minimal processing power so as to avoid data processing hardware costs, while still accomplishing gas detection having the aforementioned safety standards and minimized false alarms.

Having a properly calibrated gas detection system is important to human safety. Calibration equipment can be expensive and may mitigate against efforts to keep the cost of a gas detection system down. Accordingly, it is desirable to minimize the cost of calibrating a gas detection system.

Another cost related aspect of gas detection systems is the way in which visual indications of concentration levels and visible alarms of toxic concentrations of gas are presented to an observer of the gas detection systems. Visible meters and gauges, either having analog or digital display means, tend to be costly and could mitigate against wide spread purchase and use of such detection systems. Accordingly, it would be an advance in the art to provide a lost cost visible gas detection alarm. One such an application in need of CO gas detection is in recreational vehicles where fuel combustion is taking place.

BRIEF SUMMARY AND OBJECTS OF THE INVENTION

Given the current problems in the state of the art, it is an object of the present invention to provide a system and method for the detection of gas which approximates the concentration level of a gas and the duration of the exposure to the gas at the concentration level, where the concentration and the duration are used to avoid false alarms by determining if a true hazardous condition exists, and if so, to set an alarm.

Another object of the invention is to provide for a gas detection method and system that avoids false alarms to hazardous exposure to toxic gas by detecting the concentration level of essentially only the specific gas sought to be measured, by avoiding the detection of extraneous organic compounds and other gases, and by compensating for the effects of ambient temperature on gas concentration detection.

A still further objective of the present invention is to provide for a gas detection method and system that incorporates in an electronic circuit means a sensor element having a surface upon which a specific gas catalyzes optimally in a specific temperature range, which sensor element is designed to maximize power efficiency by minimizing the thermal mass of the sensor element, minimizing the heat-up and cool-down cycle time required to maintain proper gas catalyzing with minimized impurities, and maximizing the number of readings of gas concentration over a period of time.

Yet another further objective of the present invention is to provide for a gas detection method and system that avoids false alarms to hazardous exposure, which is capable of giving a visible indication of concentration levels of an identified toxic gas, as well as giving an audible alarm in serious gas toxicity concentrations, and is essentially efficient in power consumption, inexpensive to manufacture, and has a long useable life as compared to prior art gas detection methods and systems.

Another object of the invention is to provide a gas detection system that minimizes the cost of calibrating the same by incorporating therein a self-calibration subroutine.

It is another object of the invention to provide for a gas detection method and system that is calibratable to accurately determine the presence of specific levels of concentration of an identified gas and give a visual indication on a display means at each such level of concentration, which display means is designed to minimize the cost of providing same.

An additional objective of the present invention is to provide for a gas detection method and system that avoids false alarms to hazardous exposure while also constantly monitoring the proper functioning of the gas detection system, and has a visual display indicating when the system has malfunctioned.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, there is provided a sensor element of low thermal mass upon which a gas desired to be measured as to concentration catalyzes at and above a predetermined temperature. The sensor element is preferably enclosed in a charcoal covering to filter out extraneous gaseous matter and impurities from contact therewith.

The sensor element is associated with data processing circuitry in the inventive gas detection system, which circuitry has stored in a memory array therein gas concentration data, and has stored in a program memory means the software to process the gas concentration data. A portion of the gas concentration data is specific to the particular installed sensor element, which portion of data is acquired during an initial calibration procedure conducted at a time prior to placing the gas detection system into service.

The calibration data is a collection of both how the particular sensor element electrically responds to an exposure to a series of predetermined gas concentrations, as well as its response to ambient temperature. Thus the memory array has stored therein calibration values indicative of gas concentration levels and temperature compensation data that enable the inventive gas detection system to be calibrated to the particular sensor element and associated circuitry installed therein.

The sensor element is cyclically heated by application of electrically power to a heater element, which heater element brings the sensor element up to the predetermined gas concentration measurement and catalyzing temperature. At the predetermined temperature, a measurement of the concentration level of the gas is taken by comparing the signal from the sensor element, after digital conversion of same, to the calibration data in the memory of the inventive gas detection system.

The value obtained from the measured concentration of gas is stored in the last position of a concentration level memory array having a plurality of such positions to store concentration level measurements. When the last position in the memory array stores a new value, the first position in the concentration level memory array is discarded and replaced with the value in the second position in the concentration level memory array. Thus, a 'moving window' showing the history of measured gas concentration levels is kept in the concentration level memory array using a first-in-first-out scheme.

A sum is taken over the concentration levels in the concentration memory array. The sum over the array corresponds to a gas exposure over a period of time. If the sum of the concentration level memory array is indicative of an imminent toxic concentration of the identified gas, both an audible alarm and a visual indicator will be exhibited by the inventive gas detection system. The measured and stored level of concentration of the identified gas is visually displayed, preferable using a three-color LED, where red and green sequential color patterns are indicative of the detected concentration level of the identified gas.

After the inventive gas detection system is energized, a test is automatically and repeatedly performed to verify that the system has not malfunctioned. With respect to such automatic testing of the system, the testing constantly scrutinizes the system in a cyclical period of time so as to test most operations of the system and most probable fault conditions during each cyclical period of time. By way of example of such automatic testing, should the sensor element of the system become damaged, the data processing aspect of the system will detect the failure and cause visible indicia of the fault to be displayed with the three-color LED in predetermined patterns of red, green or orange, which may also be accompanied by predetermined audible alarms. Other testing is also performed to detect, with cyclic rapidity, the existence of malfunction conditions.

In addition to the automatic testing, a manually operable test button is provided to enable the testing of all functions of the system that are not automatically tested by the system. By depressing the test button, a pseudo alarm condition is presented by the inventive gas detection system to the user that simulates an CO exposure level to a human that would result in a ten percent (10%) carboxyhemoglobin (COHb) condition. The pseudo alarm condition is accomplished without affecting the normal operation of the gas sensor in detecting the concentration level of CO present in the ambient and without destroying concentration data previously accumulated and stored in memory. Thus, the test button procedure will not cause any reset to previous gas concentration data that was previously stored. As such the manual test will cause no danger to occupants of the area being monitored who may have been exposed to previously measured and stored concentrations of CO prior to the time that the test button was depressed.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which:

FIGS. 6A-1, 6A-2, 6A-3, 6B-1, 6B-2, 6B-3, 6B-4, 6C-1, 6C-2, 6D, and 6E taken together illustrate a flow chart showing one presently preferred method for programming the digital processor of the electronic circuit means to function as subroutines for programming illustrated by FIG. 5 in accordance with the method of the present invention.

FIGS. 7A, 7B-1, 7B-2, and 7C taken together illustrate a flow chart showing one presently preferred method for programming the digital processor of the electronic circuit means to function as subroutines for programming illustrated by FIGS. 6A-1, 6A-2, 6A-3, 6B-1, 6B-2, 6B-3, 6B-4, 6C-1, 6C-2, 6D, and 6E in accordance with the method of the present invention.

DETAILED DESCRIPTION OF THE PREFERRED EMBODIMENT

The following detailed description is divided into two parts. In part one the overall system is described, including a description of the hardware comprising the gas detection system in reference to FIGS. 1 and 2A through 2C. In part two the method by which the system of the present invention is used to electronically monitor, display and automatically record gas level concentration data is described, including a detailed description of one presently preferred method for programming the digital processor used in the electronic controller by reference to FIGS. 3 through 7C.

I. THE SYSTEM

A. The Presently Preferred Gas Detection System and Electronic Controller: FIGS. 1 and 2A through 2C The system of the present invention is comprised of a means for detecting a concentration level of a gas and for outputting an electrical signal proportional to the concentration level of the gas. The gas sensing means is placed in fluid communication with the gas so as to sense the same.

The system also includes means for converting the signal output from the gas sensing means into a series of corresponding digital signals. Also included is a digital processor means for processing the digital signals by performing a series of steps that electronically monitor, display and record gas concentration level data for the gas that is in fluid communication with the gas sensing means.

The series of steps performed by the digital processor means are deriving data from the digital signals which represents a concentration level of the gas that is in fluid communication with the gas sensing means, electronically storing all the derived data for later retrieval and calculations, and automatically displaying a representation of the gas concentration level in a visually perceptible manner to a system user once a predetermined number of gas concentration level measurements have been made, where each display measurement exceeds a selected minimum concentration level threshold.

The system also includes a data memory means for storing the digital data derived by the digital processor means for later retrieval and output, and includes a program memory means for storing machine-readable instructions utilized by the digital processor means to carry out the programmed steps.

Visibly perceptible data is shown to the system user via a display means which is electrically connected to the digital processor means, and is used to output a visual display of the concentration level of the gas that is in fluid communication with the gas sensing means.

Figure 1:
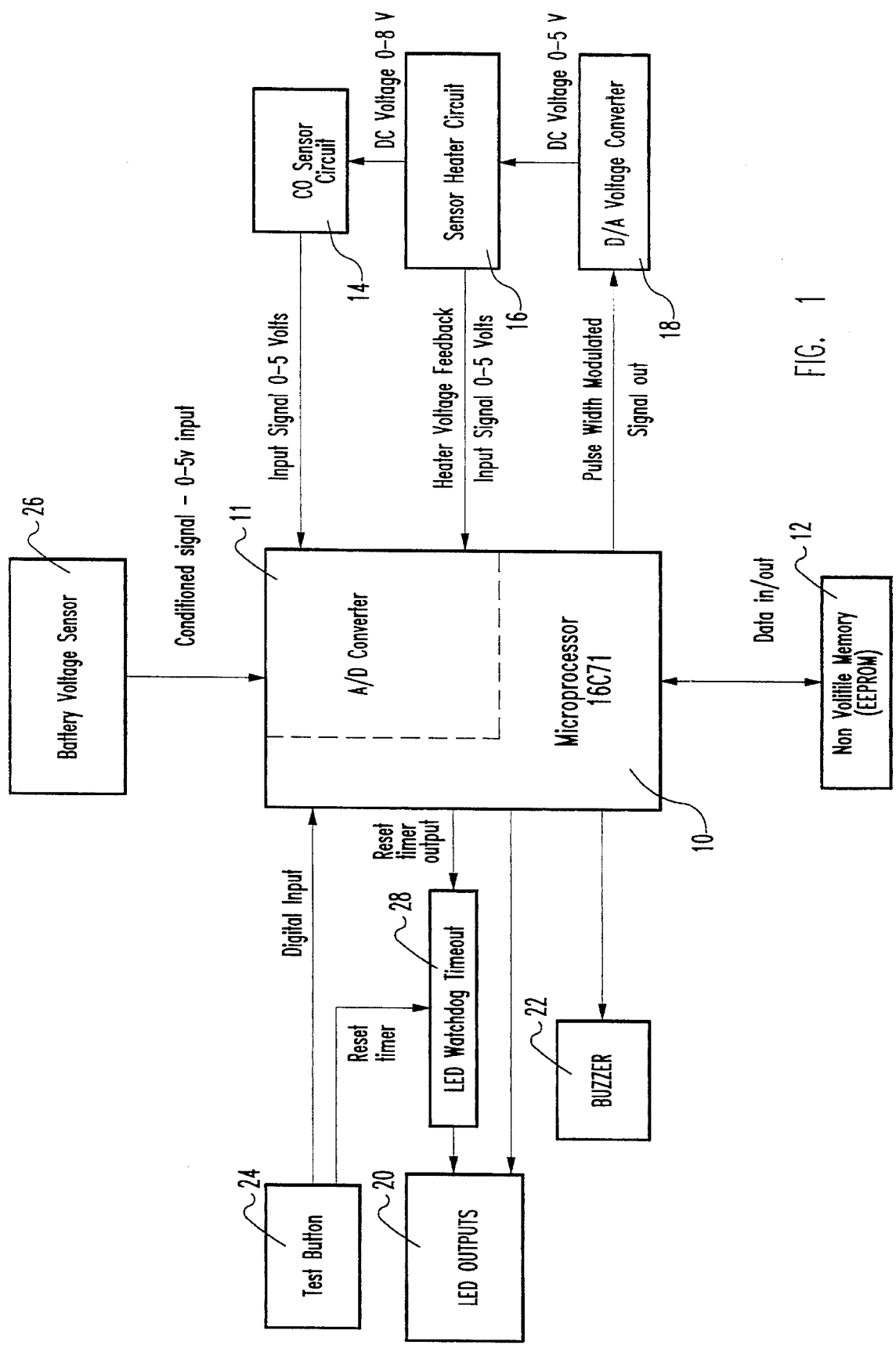
FIG. 1 is a functional block diagram which schematically illustrates the primary components of one presently preferred electronic circuit used in connection with the electronic circuit means of the system and method of the present invention.

FIG. 1 shows a functional block diagram of one embodiment of the hardware of the inventive gas detection system. A 16C71 microprocessor 10, which is a low cost limited storage capability controller, has an A/D converter 11 associated therewith. Microprocessor 10 is in electrical communication with an EEPROM 12 which keeps data in nonvolatile memory for use after a power down of the gas detection system.

A/D converter 11 receives input from a CO sensor circuit 14. A voltage is applied for a specific duration to heat up the CO sensor circuit by a sensor heating circuit 16. Sensor heating circuit 16 receives input from a D/A voltage converter 18, the later being controlled by microprocessor 10 via a pulse width modulated signal therefrom.

Microprocessor 10 controls a three color LED 20 which serves to visually display an indication of the detected gas concentration levels, to prompt the system user during calibration of the gas detector system, and to indicate system fault conditions. Also controlled by microprocessor 10 is an audible alarm 22 which serves to audibly indicate dangerously high gas concentration exposures, as well as system fault conditions. The power supply to the system, such as a battery, is monitored by a battery voltage sensor 26 to detect an adequate power supply or absence thereof for the energizing of the gas detection system. An LED watchdog timeout circuit 28 is associated with a system fault monitoring process to continually ascertain the integrity of the gas detection system and to set LED 20 to a predetermined color pattern to indicate the occurrence of a fatal malfunction.

The functional block diagram of FIG. 1 can be implemented by the circuitry depicted in FIGS. 2A through 2C, the components thereof being more fully described in Table I, below. The artisan will understand that different circuit designs are possible to implement the functional block diagram of FIG. 1. Thus, FIGS. 2A through 2C and the component list of Table I are offered only for purposes of illustration and not for purpose of limitation of the inventive method and system of gas detection.

Figure 2A:
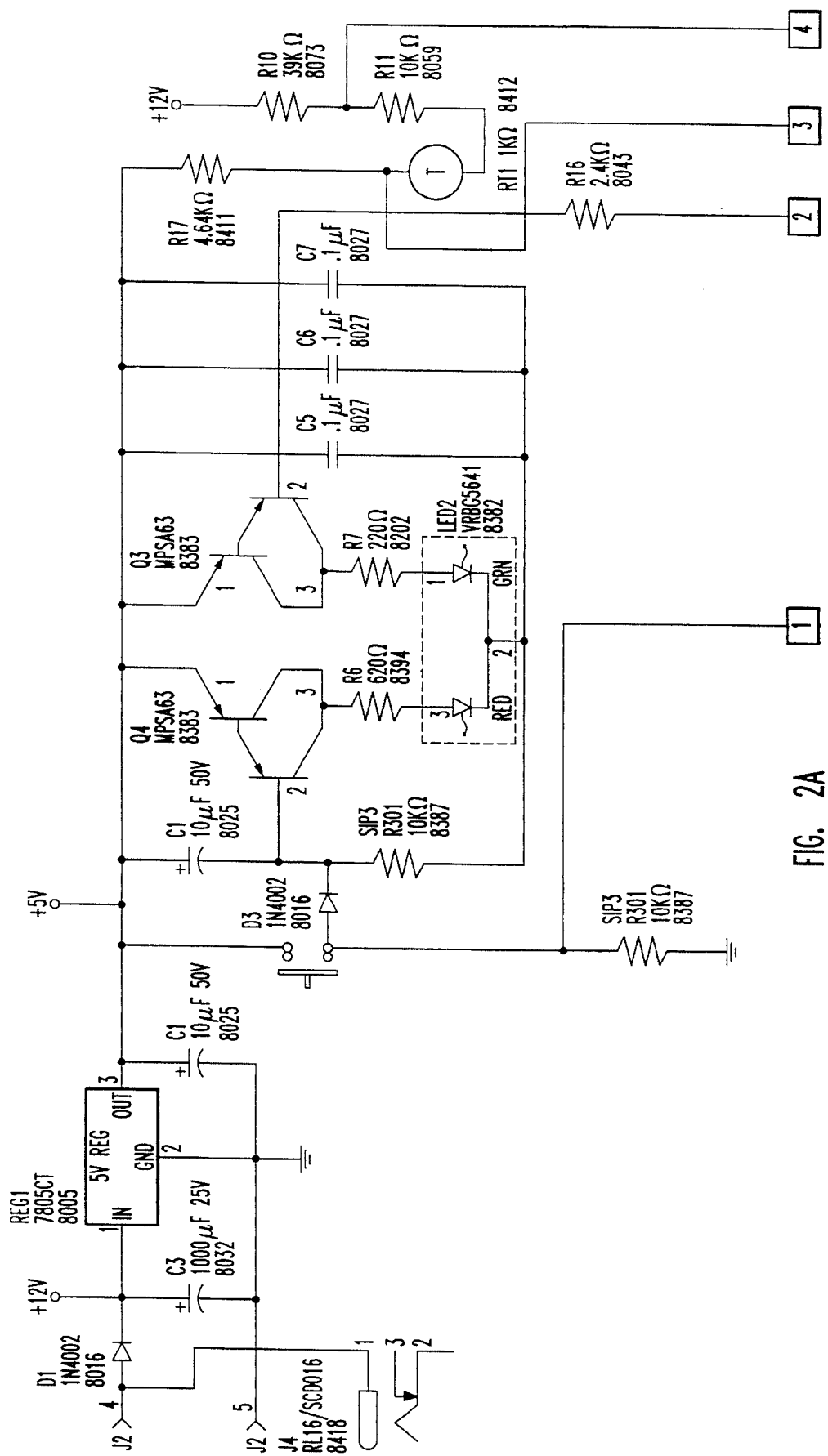
FIGS. 2A through 2C taken together constitute a detailed electrical schematic diagram which illustrates, as an example, the presently preferred embodiment and presently understood best mode for implementing the electronic circuit means of the system and method of the present invention.
Figure 2B:
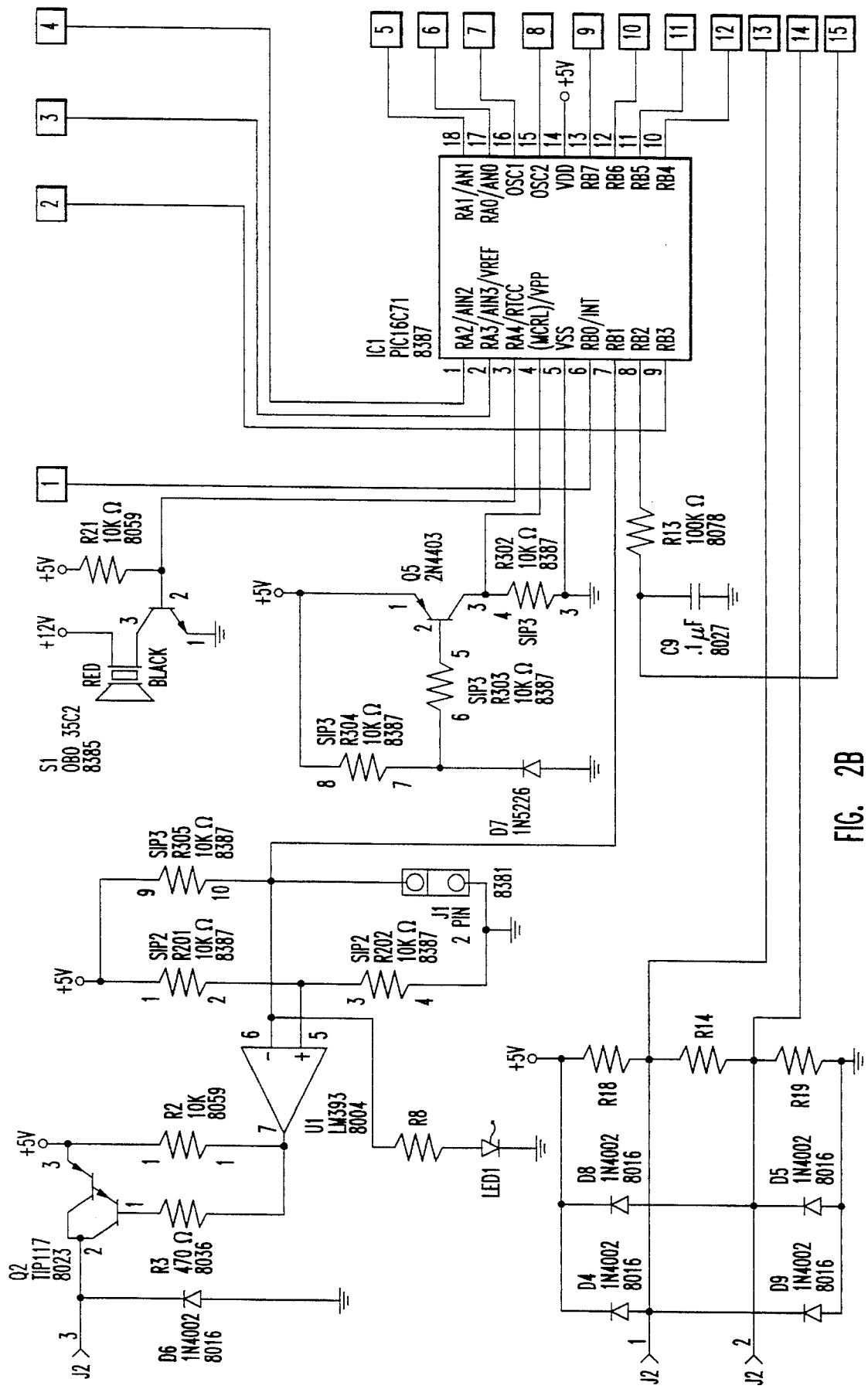
Figure 2C:
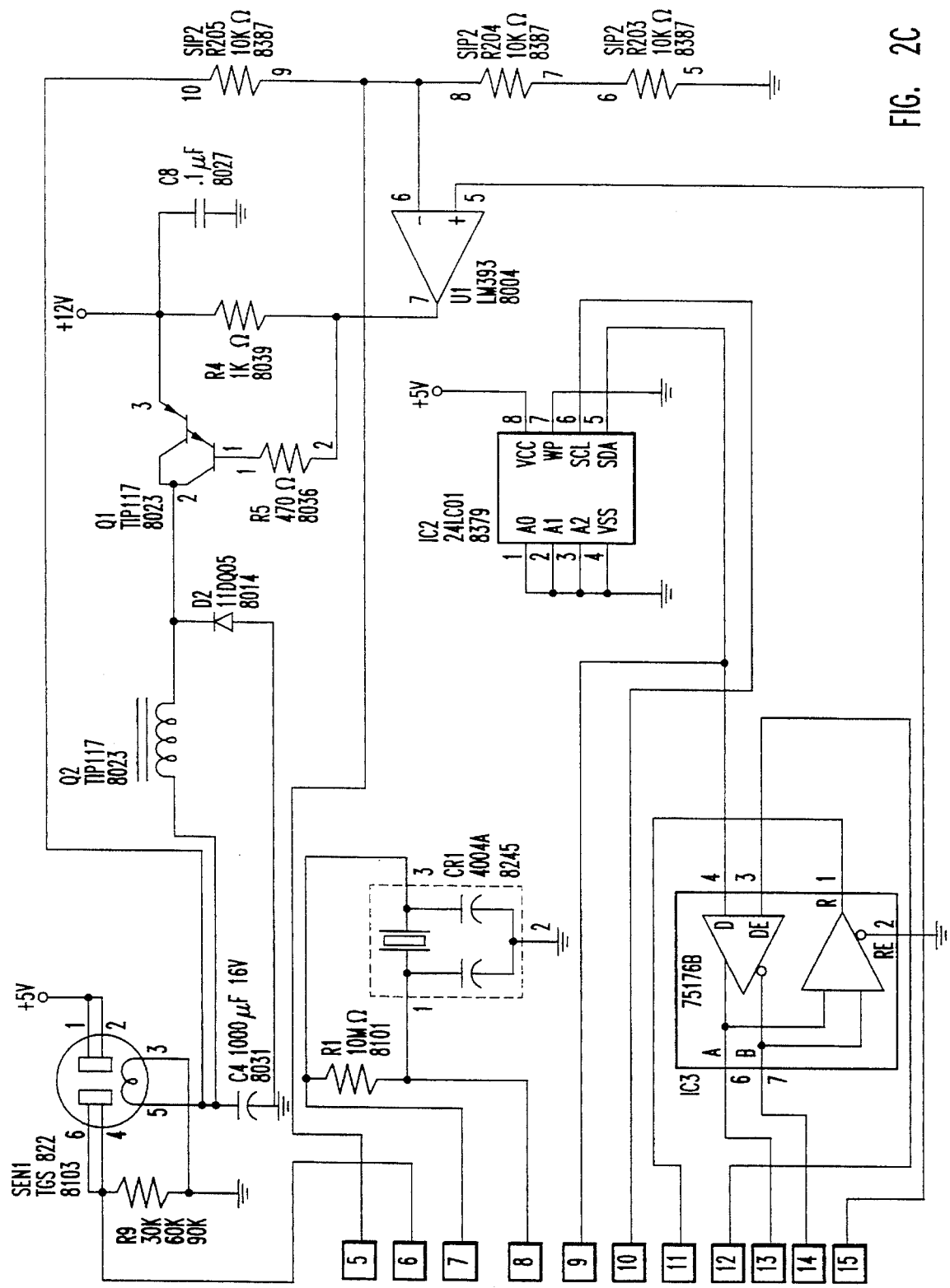

The electrical schematic of FIGS. 2A through 2C illustrates the presently preferred gas detection and monitoring system which is designed to detect dangerous levels of CO in confined areas, such as recreational vehicles or residential areas. The circuitry is preferably packaged in a plastic casing and has approximate dimensions of 3.75" high by 3" wide by 1,375" deep. The system is equipped with both audio and visual alarms, respectively a speaker S1 and a three-color LED2. Additional features include non-alarm CO concentration level visual signaling with LED2, an alarm silence feature, and a real time self diagnostic reporting capability with speaker S1 and LED2. An audio alarm, using speaker S1, will sound before the CO concentration over time would cause a theoretical person to have a blood condition of approximately 10 percent carboxyhemoglobin (COHb).

The power supply of the system is intended to supply 12 volts of DC power. Power is fed to the unit through a diode D1 to prevent damage due to a reverse connection of power leads during installation. A 1000 uF electrolytic capacitor is used for both AC connections and poorly filtered DC converters, such as are typically used in recreational vehicle installations. The 12 volts is then regulated to 5 volts by REG1, a LM7805 5 V regulator. C1, a 10 uF electrolytic capacitor, is used to improve the transient response of the 5 V regulator.

Shown in FIGS. 2B and 2C are IC1, R1 and CR1 which together form the microprocessor control system (MCS). CR1 is a 4 Mhz ceramic resonator that, when coupled to microprocessor IC1, creates a 250 nanosecond clock resulting in a 1 microsecond instruction execution cycle. All microprocessor instructions execute in 1 or 2 instruction cycles (1–2 microseconds). This allows for real time control of the switching of the power supply and all other gas detector operations.

Preferably, a Figaro Model No. TGS-822 gas sensor SEN1, as modified by placing an active charcoal filter, screen and cap thereover, is used as the gas sensor. A resistor R9 is coupled to gas sensor SEN1, which together with SEN1 form a voltage divider network where the voltage increases proportionally with increases in CO exposure. Sensor SEN1 has a low thermal mass semiconductor sensor element that is designed to detect alcohol and other hydrocarbons. However, when modified as stated above in combination with a prescribed heating cycle, sensor SEN1 detects CO.

A digital-to-analog conversion is achieved by pulse width modulating an RC integrator, formed by R13 and C9 and is designed to operate the sensor heater circuit 16 at 0 to 8 volts. The output of RC integrator R13, C9 feeds into the negative input of the switch driver circuit, which is described below. Pulse width modulation is determined by reading the feedback voltage to the positive input of the switch driver circuit. If the feedback voltage is too high, the output pin to RC integrator R13, C9 is turned off. If the feedback voltage is too low, the output pin is turned on.

The switch driver circuit is the first stage of a comparitor U1 (LM393), voltage feedback resistors R203, 204 and 205, an inductor L1, and a capacitor C4. The output of comparitor U1 connects to a pnp power Darlington transistor Q1 which acts as a switch for the 12 volt power supply. The switched voltage output of transistor Q1 feeds into inductor L1. Inductor L1 performs no significant function except when the line voltage drops below 8 volts, at which time inductor L1 then acts as an energy storage device to allow continued operation of sensor SEN1. Capacitor C4 acts as a filter and voltage integrator by maintaining an even, low ripple voltage across the heater element.

The regulation technique of the system incorporated microprocessor IC1 maintains the required output voltage for the heater element to the negative input of comparator U1. Comparator U1 monitors the negative terminal input voltage provided by RC integrator R13, C9 and the positive terminal input voltage feedback from capacitor C4. By comparing the voltage between the two input terminals, comparator U1 either turns transistor Q1 on or off. On initialization, microprocessor Ic1 will charge RC integrator R13, C9, causing the output of comparator U1 to go low, thus turning transistor Q1 on, which allows capacitor C4 to charge. While microprocessor IC1 maintains the voltage of RC integrator, comparator U1 waits for the voltage feedback from capacitor C4 to exceed the voltage of RC integrator R13, C9, then sets the output to high, turning off transistor Q1. Capacitor C4 then discharges. When capacitor C4 feedback voltage drops below the RC voltage, transistor Q1 is turned on again to make up the charge.

CO detection by sensor SEN1 requires 6 volts to be applied as a 'catalyzing off' or 'cleaning' cycle, removing all undesirable reducing or oxidizing gases that catalyze upon the surface of SEN1 at high temperature. After such cleaning by catalyzing off at an elevated temperature, 3 volts is applied to SEN1. The applied voltage is a heat producing voltage that allows the sensor element of SEN1 to catalyze CO, causing a rise in the sensor element conductivity.

Line voltage monitoring is accomplished by a voltage divider network that is formed by resistors R10 and R11. Microprocessor IC1 reads the voltage at the divider junction by analog-to-digital conversion. Line voltage monitoring by microprocessor IC1 occurs in the last second of the 58 second 6 volt cycle. Error level in line voltage detection occurs at 10 V DC.

A non-volatile memory is found in FIG. 2C at IC2, where data is transferred by a synchronous serial communication between microprocessor IC1 and nonvolatile memory IC2.

An audio alarm annunciator is also found in FIG. 2B, which is a piezo-electric alarm S1 which is controlled by microprocessor IC1 through transistor TR1 which is a bipolar 'npn' transistor. When transistor TR1 is turned on, 12 volts is applied across speaker S1, sounding the audible alarm.

A visual alarm and fault display is available to the system user as a diagnostic tool and output means. The alarm and display consist of transistors Q3 and Q4, resistors R6 and R7, and three-color LED2. Resistors R6 and R7 are current limiting resistors to protect elements of LED2 from burning out. Transistors Q3 and Q4 allow control of the red and green elements of LED2 by microprocessor IC1. For a green LED condition to display, microprocessor IC1 must be functioning at initialization of the gas detector system when power first energizes the system.

The inventive gas detection system includes both internal and external watchdog circuits. In the internal watchdog circuit, packaged within microprocessor IC1 is a free running on-chip RC oscillator that does not require external components. The firmware program resets the internal clock or timer of microprocessor IC1 at every execution of the main program loop. Should microprocessor IC1 stop functioning or its external ceramic oscillator CR1 stop functioning, a time-out will occur which will cause the resetting of microprocessor IC1.

In the LED watchdog circuit 28 shown in FIG. 2A, an external RC timer created by capacitor C2 and resistor R15 controls the function of the red LED element in LED2. To prevent the red LED element of LED2 from being displayed, microprocessor IC1 must periodically remove the charge stored in capacitor C2 in order to prevent a red LED signal in LED2. If microprocessor IC1 fails to clear the charge that is stored in capacitor C2, a solid red or orange LED signal is displayed on LED2 to indicate a non-recoverable system error to the system user.

The circuitry of FIGS. 2A through 2C can be programmed to perform a particular method of gas concentration detection as follows. Gas detection occurs during the last second of a 30 second 3 volt heater voltage cycle. Catalyzing of CO gas on SEN1 sensor element will cause an increase in sensor element electrical conductivity and an increase the voltage read by IC1 via analog-to-digital converter 11 in FIG. 1. Microprocessor IC1 will compare the voltage level detected to previously stored calibration values maintained in non-volatile RAM IC2. If CO levels that are above the lower calibration limit are encountered, microprocessor IC1 will calculate the exposure level and maintain a total exposure record over the last 60 CO concentration readings. Integration occurs in a 90 minute sliding window, where the window contains the last 60 CO concentration readings. Readings older than 90 minutes are subtracted from the sum of the last 60 concentration values, and the newly read concentration value is added to the sum of the last 60 concentration values. An audible alarm by speaker S1 occurs when the sum of the last 60 CO concentration level readings exceeds a predetermined sum which approximates a 10% COHb level in a theoretical person's blood who had been breathing a predetermined concentration of CO over a predetermined amount of time.

Also present in FIGS. 2A through 2C are certain controls and displays that allow a system user to manually initiate a test that monitors and reports upon the proper functioning of the gas detection system. A test button SW1 is provided to test the system's operation. Test button SW1 must be pressed for a predetermined number of seconds before the test function activates. Test button SW1 resets the external watch dog circuit, as described above. Such a test will result in a shutdown of the green LED display in LED2 and an audible alarm signal of S1 for 4 minutes, 15 seconds. Once test button SW1 is released, LED2 will display a visual color pattern. Pressing button SW1 again during a test cycle will return the system to normal operation. Test button SW1 provides a dual function as an audible alarm silencer. If button SW1 is depressed for 3 seconds during an audible alarm condition, the audible alarm will silence for 4 min 15 seconds, but the visual alarm will still operate once button SW1 is released.

The visible indicator of CO concentration is LED2. Using LED2, the system is capable of displaying the relative exposure level of CO it is monitoring, which is a function of both time and concentration of CO. LED2 will flash in accordance to the following color pattern every 8 seconds at a 1 Hz frequency, relative to the concentration of CO detected as follows:

| | |
|---|---|
| 0–100 ppm | Solid Green LED |
| 100–200 ppm | Green with 1 red flash |
| 200–400 ppm | Green with 2 red flashes |
| 400–800 ppm | Green with 4 red flashes |
| above 800 ppm | Alternating red/green flash |

FIGS. 2A through 2C feature both fault and alarm display capabilities, where the fault signals fall in two categories which comprise both audible and visual fault signal. The audible fault signal of the system is a solid tone from S1 or a "chirp" occurring every 88 seconds. Under no circumstance does the operation of the software allow a continuous tone. Visual signals are of four types: solid orange at LED2, solid red at LED2, no color at LED2, and an orange/green flashing at a LED2. Of the four visual signals, the first three are fatal and indicate the gas detection system will not function as intended or will not function at all. The fourth visual signal is unique as it is a result of line voltage monitoring and is displayed to indicate to the system user a deficiency in power in the system's power supply. This is not a fatal error and will have no effect on the operation of the system. Should the voltage drop from the power supply down to a range that the system will not function, one of the other three codes will be displayed.

In the presently preferred embodiment, microprocessor IC1 may be a general purpose microprocessor or an equivalent device. Alternatively, it may be desirable to utilize a more powerful microcomputer, such as an IBM personal computer, to devise a microprocessor-based apparatus specifically designed to carry out the data processing functions incidental to this invention. When choosing a microcomputer, if gas sensing concentration and gas exposure over time calculations are to be carried out and displayed in real time, microprocessor IC1 or other processor means must carry out the required number of computations very quickly to satisfy real-time needs.

Importantly, the hardware which embodies the processor means of the present invention must function to perform the operations essential to the invention and any device capable of performing the necessary operations should be considered an equivalent of the processor means. As will be appreciated, advances in the art of modern electronic devices may allow the processor means to carry out internally many of the functions carried out by hardware illustrated in FIGS. 2A though 2C as being independent of the processor means. The practical considerations of cost and performance of the system will generally determine the delegation of functions between the processor means and the remaining dedicated hardware. However, a low cost processor is desirable.

Visual display LED2 performs the function of a display means. As intended herein, the display means may be any device which enables the operating personnel to observe the concentration levels and exposure values calculated by the microprocessor. Thus, the display means may be a device such as a cathode ray tube, an LCD display, a chart recorder, or any other device performing a similar function. In the preferred mode, the display means is a low cost three color LED, such as that depicted by LED2 in FIG. 2A.

II. THE METHOD

Attention is next turned to a detailed description of the presently preferred method by which the system of the present invention is used to monitor, display, and automatically record gas concentration data, with particular reference to FIGS. 3 through 5, 6A-1, 6A-2, 6A-3, 6B-1, 6B-2, 6B-3, 6B-4, 6C-1, 6C-2, 6D, and 6E, and 7A through 7C which illustrate one presently preferred embodiment of the instructions which may be utilized to control the digital processor means. As will be appreciated by those of ordinary skill in the art, and as noted above, while the system and method as described in reference to the preferred embodiments herein illustrate the system and method as implemented using state of the art digital processing design and corresponding program instructions for controlling the processor, the system and method could also be implemented and carried out using a hardware design which accomplishes the necessary electronic processing, which is thus intended to be embraced within the scope of various of the claims as set forth hereinafter.

Figure 3:
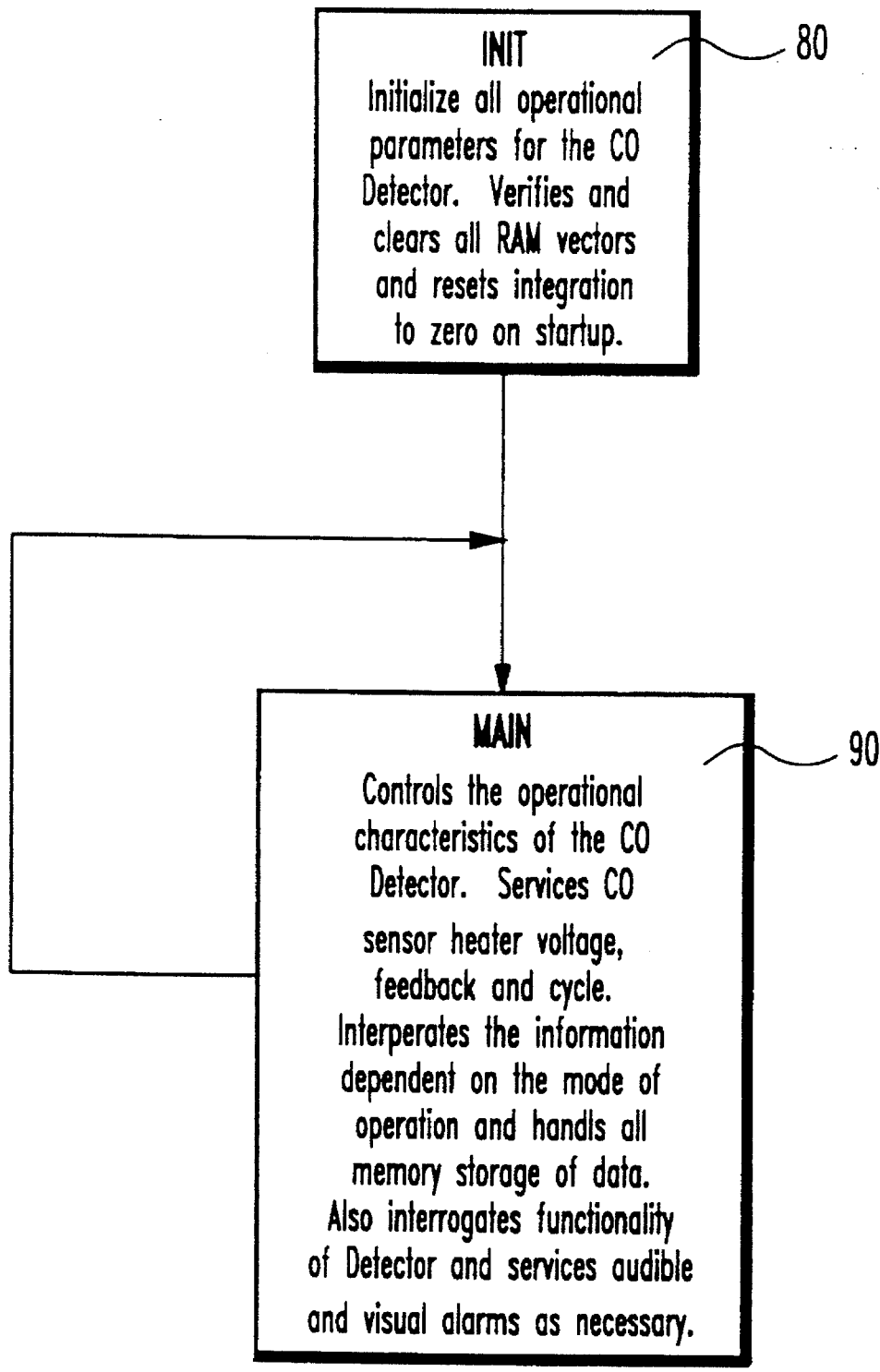
FIG. 3 is a functional block diagram which schematically illustrates the primary components of one presently preferred method for programming both the initialization mode and the operational mode of the digital processor of the electronic circuit means of the inventive gas detection system in accordance with the method of the present invention.

The method of the present invention is seen in overview in FIG. 3 which depicts a functional block diagram which schematically illustrates the primary components of one presently preferred method for programming both the initialization mode and the operational mode, which modes are performed essentially by the digital processor of the electronic circuit means of the inventive gas detection system in accordance with the method of the present invention. As seen in FIG. 3, the software programming is essentially divided into two sections: the initialization and the main execution loop. The initialization loop prepares the gas detection system hardware for the main execution loop and verifies functionality of the hardware. If an error is detected during the initialization loop, no heater voltage is applied to gas sensor. During the main execution loop, the system applies 6 V to the sensor heater for 60 second to clean sensor surface of impurities prior to CO gas detection. Then the system begins the gas detection cycle where the system applies 6 volts to the sensor heater for 58 seconds followed by 3 volts being applied to the sensor heater for 30 seconds.

A description of the steps carried out in FIG. 3 is as follows:

Step 80: Performs an integrity check on the RAM section of the microprocessor.

Step 90: This routine is the main program loop in which the concentration of gas is sensed and data accumulated as to the concentration over time (e.g. exposure) as well as error checking as to the integrity of the system.

Figure 4:
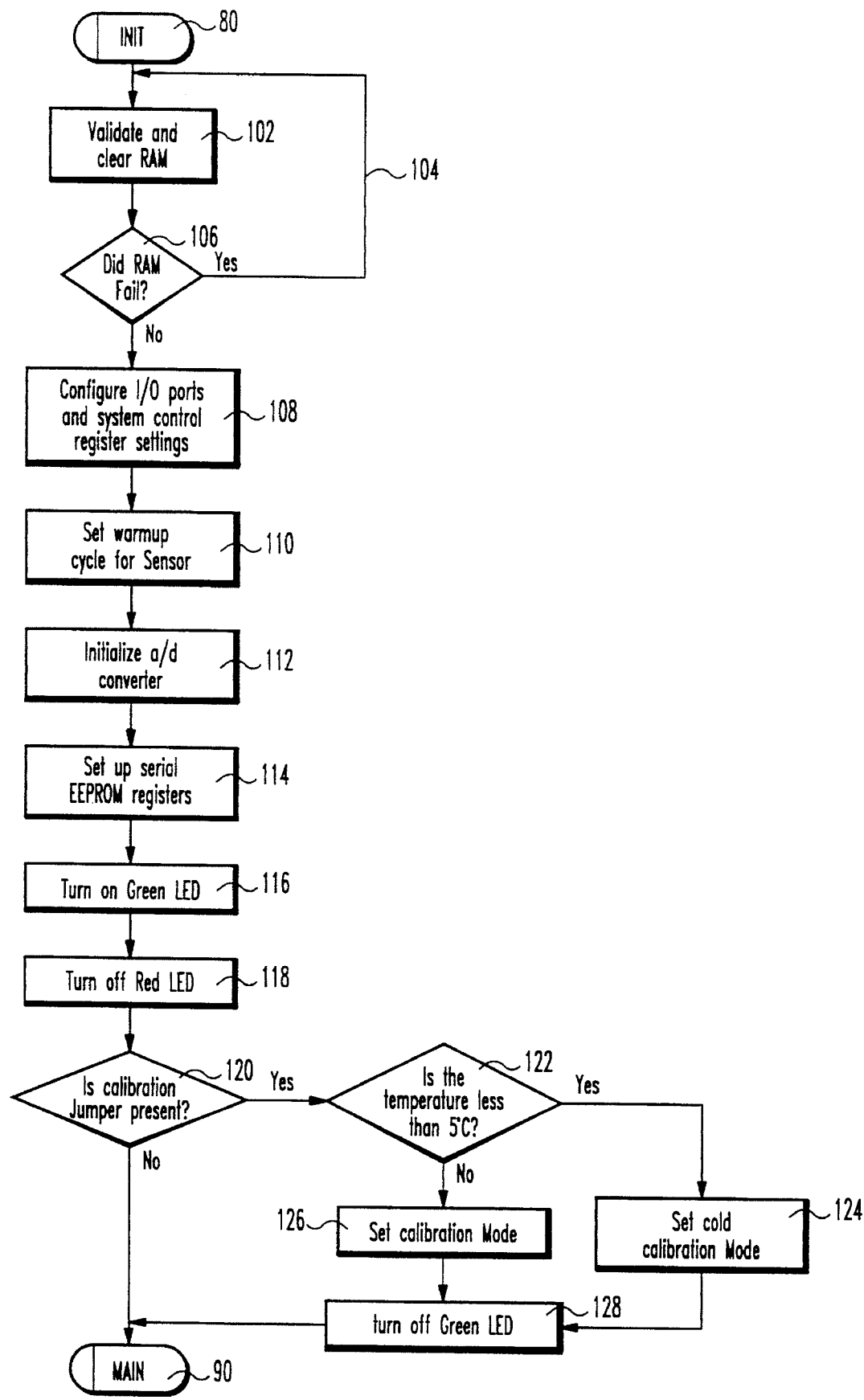
FIG. 4 illustrates a flow chart showing one presently preferred method for programming the initialization mode of the digital processor of the electronic circuit means at the start-up of the operation of the inventive gas detection system in accordance with the method of the present invention.

An expanded flow chart of the initialization mode of step 80 of FIG. 3 is set forth in FIG. 4. A description of the steps carried out in FIG. 4 is as follows:

Step 102: Initialize all RAM memory.

Step 106: Ascertain the integrity of the RAM initialization results from step 102.

Step 108: Set inputs and outputs to the microprocessor, turn on the analog to digital converter, and enable the interrupts and time scaling capabilities.

Step 110: Initialize RAM contents for operation of the sensor, including setting voltages, and period lengths which are stored in the firmware in the on-board ROM space of the microprocessor.

Step 112: Read the A-to-D converter.

Step 114: Load the initial RAM variables stored in the firmware to allow the system to communicate to the external RAM nonvolatile memory.

Step 116: Show that the power is on by turning the three-color LED to be the green color.

Step 118: Reset the external watchdog timer by disallowing the red LED to turn on.

Step 120: Check for the presence of a jumper to determine if the calibration subroutine (See step 1910) should be entered.

Step 122: for the calibration subroutine, check the thermistor to determine if a cold or a warm calibration is being requested.

Step 126: Set a flag to indicate that a warm calibration shall be executed during the calibration subroutine.

Step 128: Turn off the green LED so as to indicate that the calibration subroutine is being performed.

Step 124: Set a flag to indicate that the cold calibration mode will be executed during the calibration subroutine.

Figure 5:
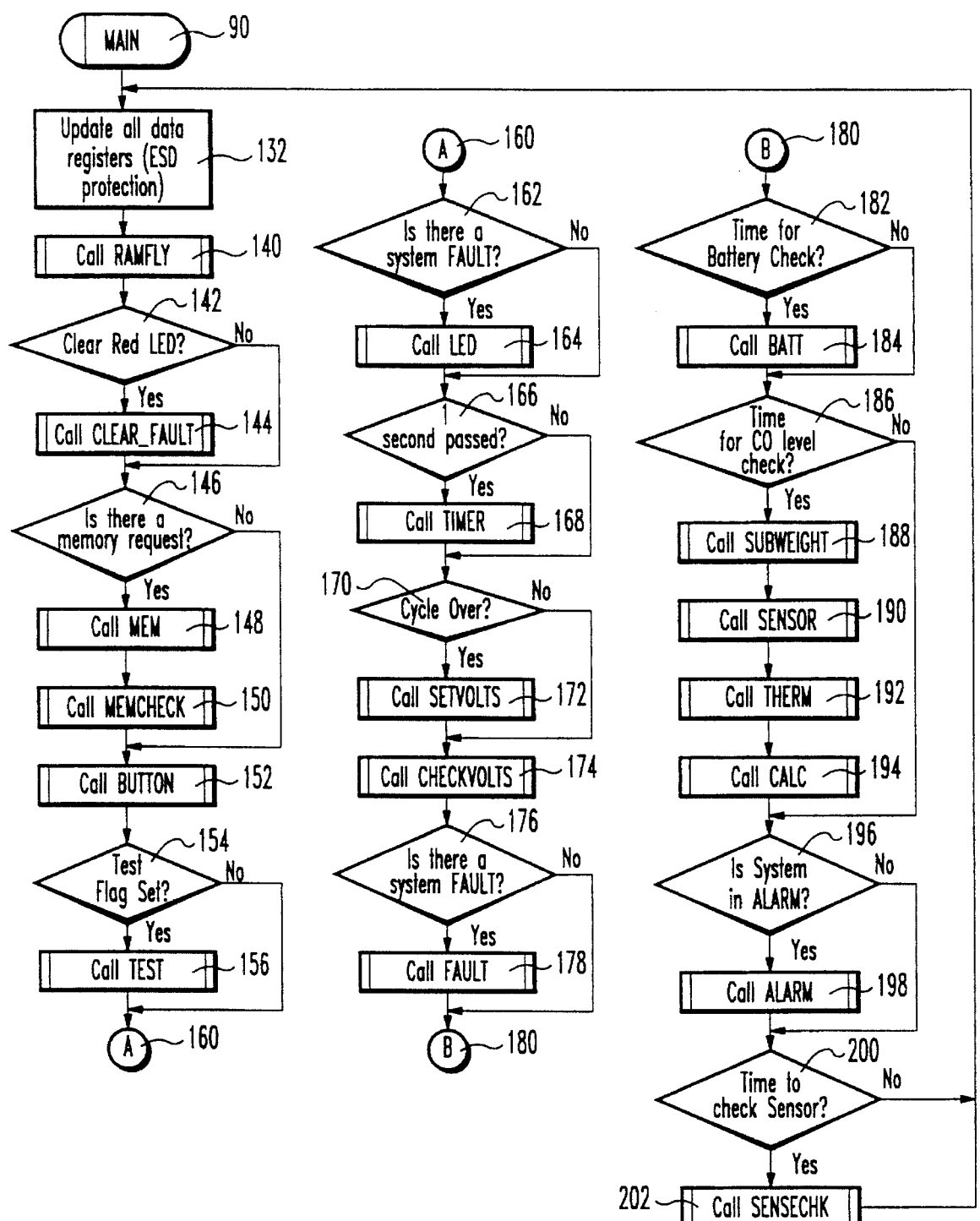
FIG. 5 illustrates a flow chart showing one presently preferred method for programming the operational mode and flow of data therein during both a calibration mode and a gas concentration detection mode in the digital processor of the electronic circuit means of the inventive gas detection system in accordance with the method of the present invention.

An expanded flow chart of the main operational mode of step 90 in FIG. 3 is set forth in FIG. 5. A description of the steps carried out in FIG. 5 is as follows:

Step 90: This routine is the main program loop in which the concentration level of gas is sensed and data accumulated as to the time of exposure thereto, as well as checking the integrity of the system.

Step 132: Refresh the critical microprocessor configuration elements.

Step 140: At this point, the ability of RAM to maintain data is checked.

Step 142: Prevent a red LED from turning on at the request of the microprocessor.

Step 144: Enables circuitry to prevent a red LED from turning on by resetting an external watchdog.

Step 146: Check to determine if the processor has requested to communicate with the external nonvolatile memory.

Step 148: Read or write to external memory, depending on the requested mode.

Step 150: Read back the last written byte.

Step 152: Determine if the test button is depressed.

Step 154: Determine if the test button has been depressed for at least three seconds.

Step 156: Determine if a red LED will come on and if the audible alarm will sound.

Step 162: Determine if the microprocessor has reported a fault condition.

Step 164: Service normal LED output routines.

Step 166: Determine if the internal timer has clocked at least one second.

Step 168: Increment all system timers.

Step 170: Determine if the requested voltage heating cycle has been completed, where a voltage heating cycle is either 58 seconds at 6 volts, or is 30 seconds at 3 volts, and where the heat is applied to the heater element.

Step 172: Set the cycle timer to 58 seconds or to 30 seconds, depending on the requested heating voltage cycle, and set the requested voltage output to 6 volts or 3 volts accordingly.

Step 174: Determine if the requested voltage has been met, where the requested voltage is either 6 volts or 3 volts.

Step 176: Determine if the microprocessor has reported a fault condition.

Step 178: Turn on a orange LED (combination of red and green colors) because the microprocessor has experienced a fatal error.

Step 182: Determine if it is time to check the battery, which check occurs every 90 seconds.

Step 184: Monitor the battery voltage to see if there is ample power in the battery.

Step 186: Determine if it is time to check the CO level, which check occurs once every 90 seconds on the 29th second of a thirty second 3 volt voltage heating cycle.

Step 188: Subtract the oldest CO level reading from the sum of the past 60 CO level readings, which sum is contained in an external nonvolatile memory array.

Step 190: Read the most current CO concentration level from the sensor.

Step 192: Adjust the gas sensor CO level reading to compensate for ambient temperature using a temperature compensation variable obtained during the calibration subroutine (See step 1910).

Step 194: Calculate an adjusted concentration level of CO given the previous CO level reading.

Step 196: Determine if a predetermined hazardous exposure to CO has been reached.

Step 198: Sound an audible alarm and flash a red LED when the predetermined hazardous exposure to CO is reached.

Step 200: Determine if it is time to check the integrity of the gas sensor, which check occurs at the end of each respective voltage heating cycle (58 seconds or 30 seconds).

Step 202: Check the gas sensor twice every 90 seconds to detect failure, which failure is indicated by a detection of 0 volts from the sensor element when 6 volts is applied to the heater element, or when 5 volts is read from the sensor element and 3 volts is applied to the heater element, where a check is made by reading the sensor element input voltage.

Figures 1, 6A:
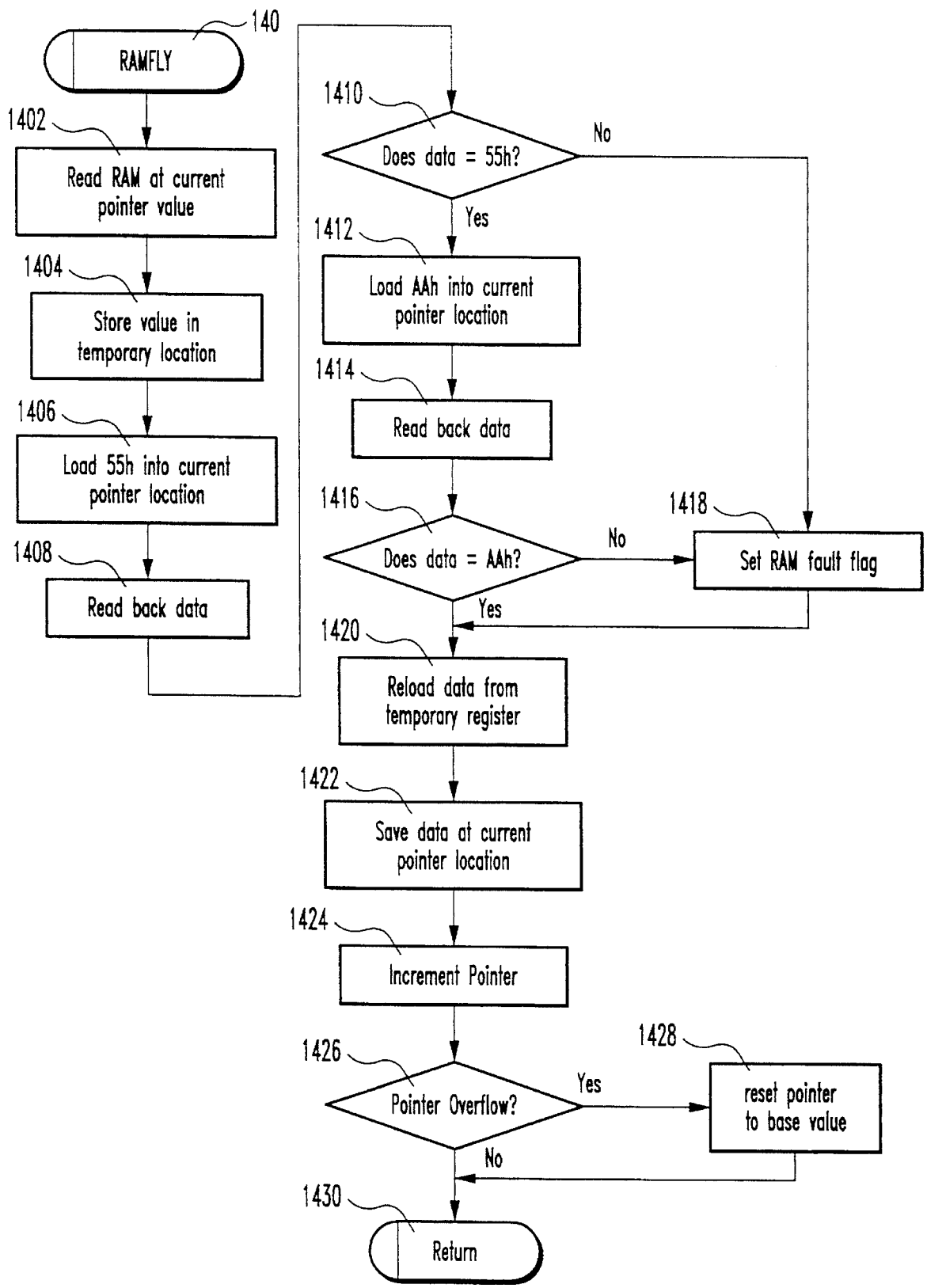
Figures 2, 6A:
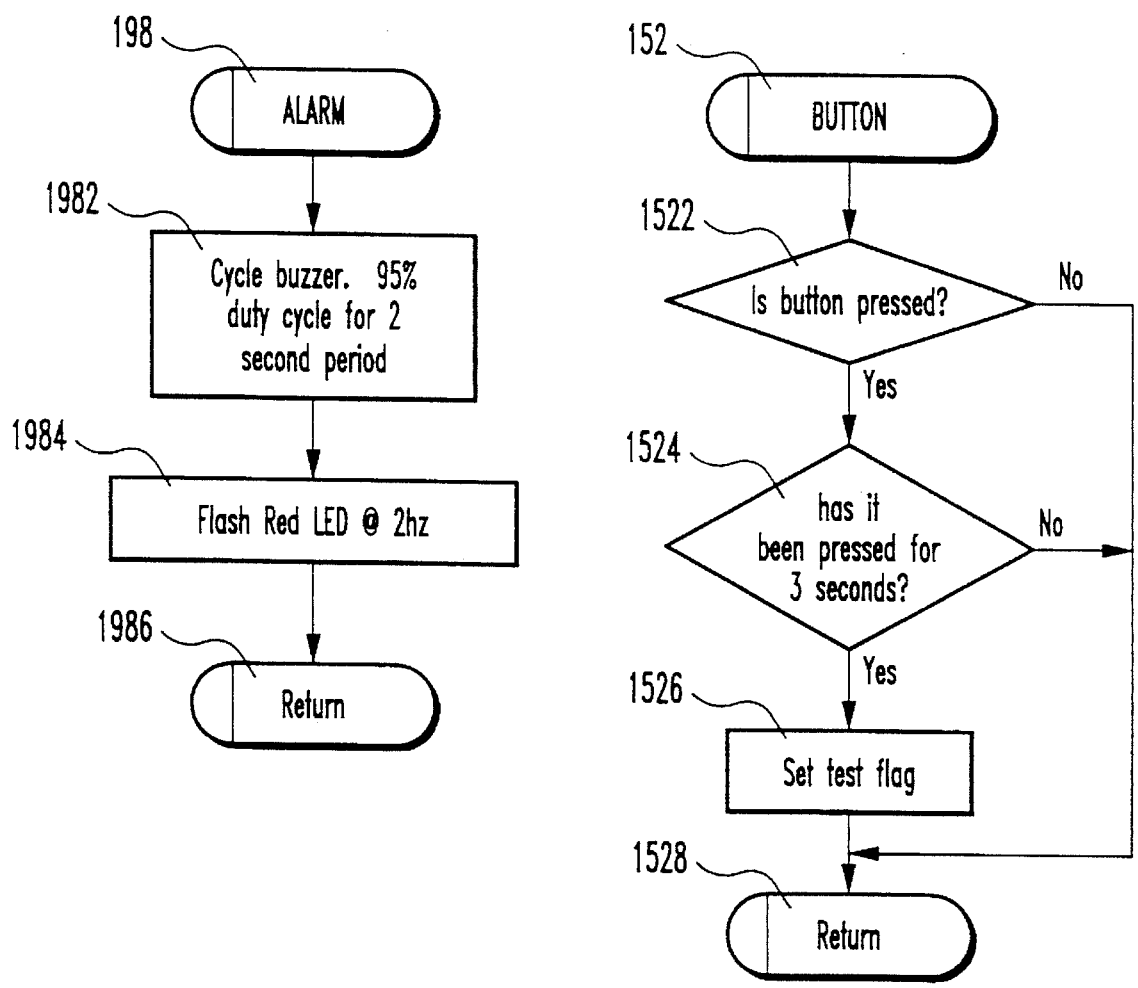
Figure 6A:
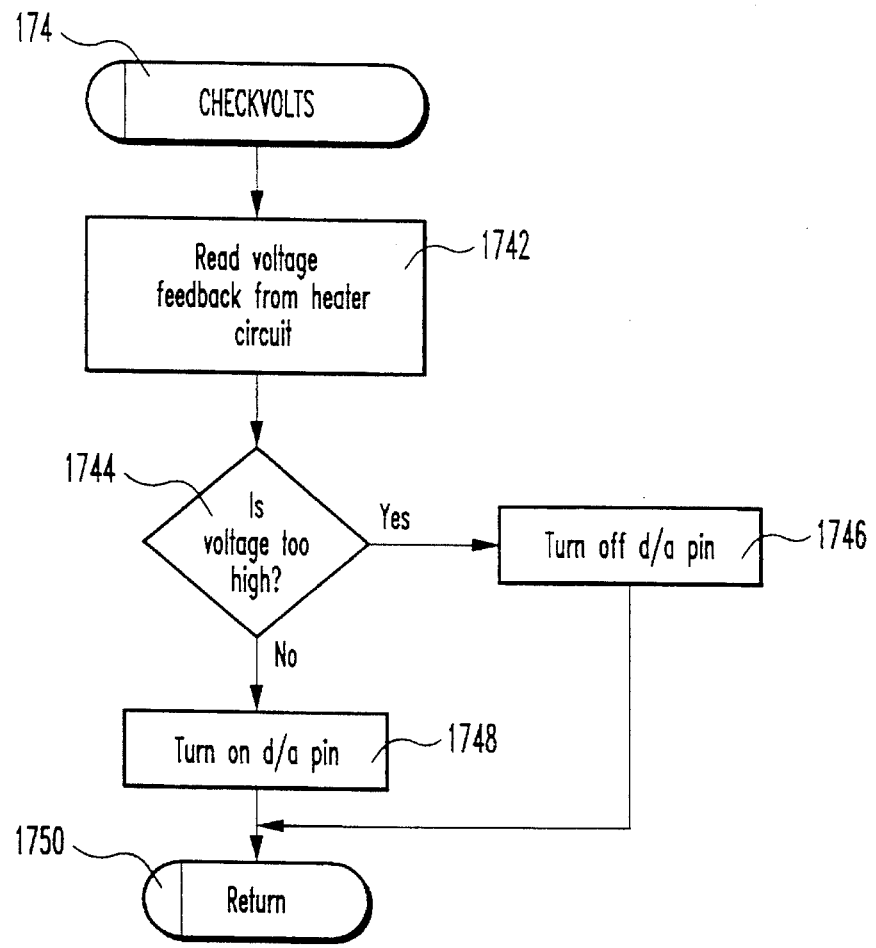
Figure 3:
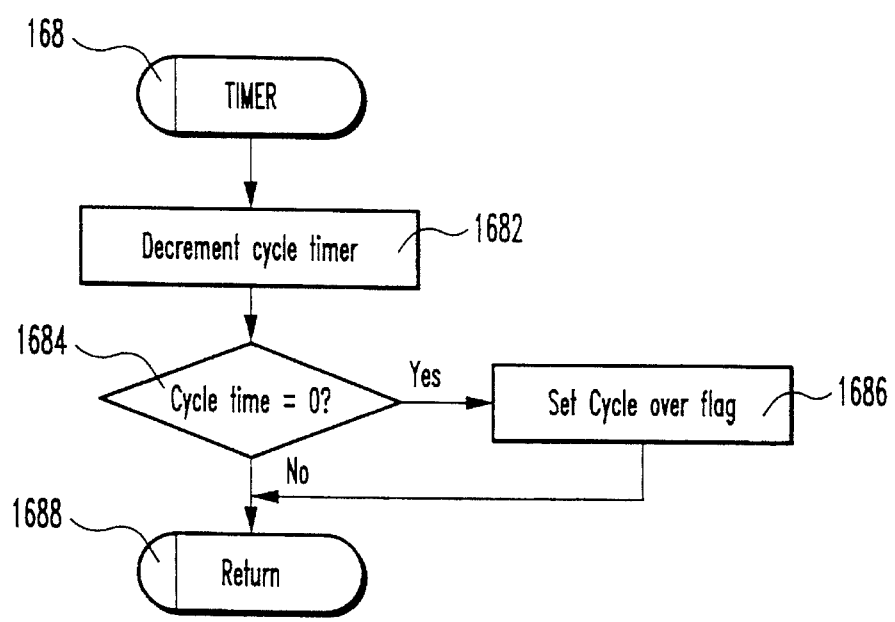
Figures 1, 6B:
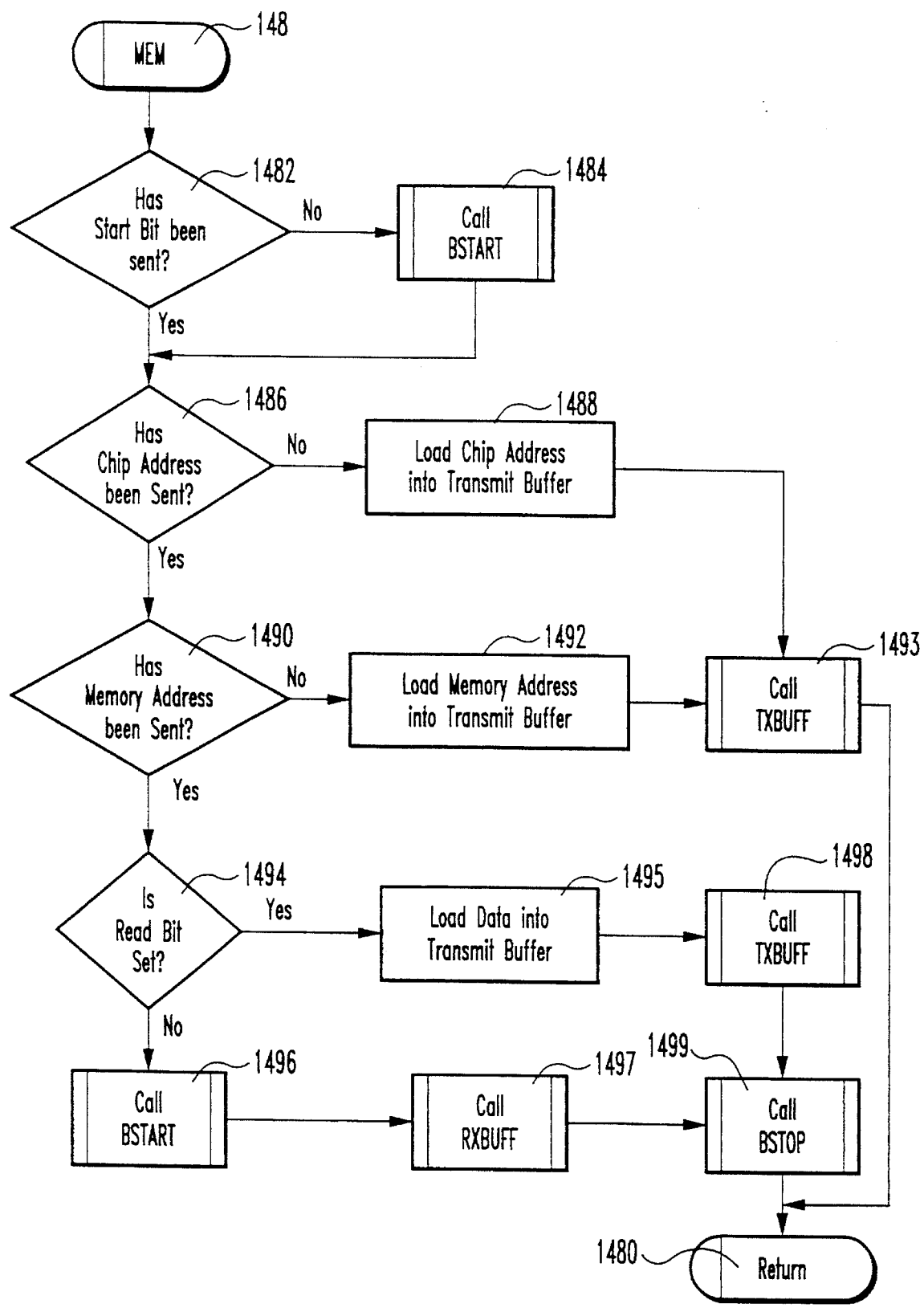
Figures 2, 6B:
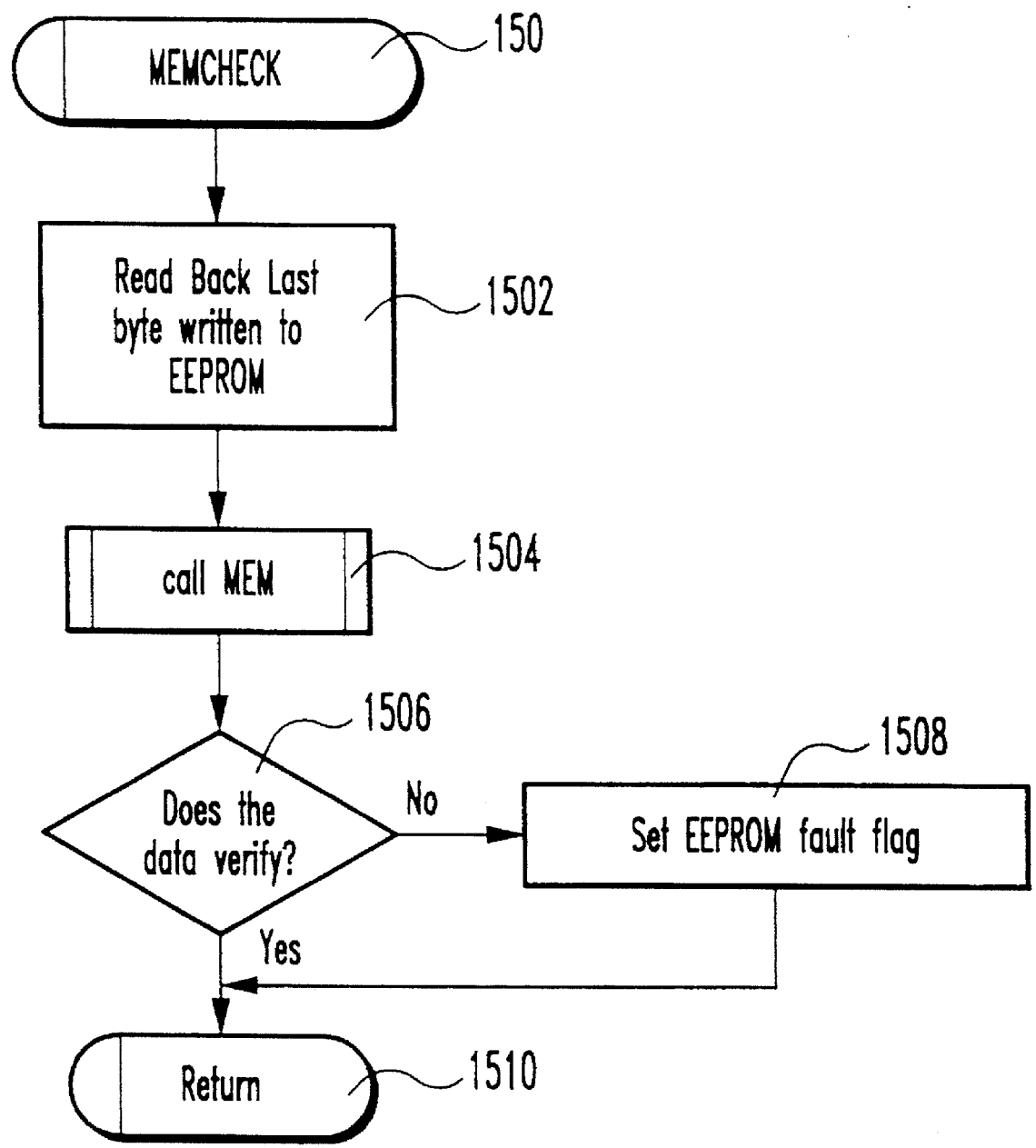
Figures 3, 6B:
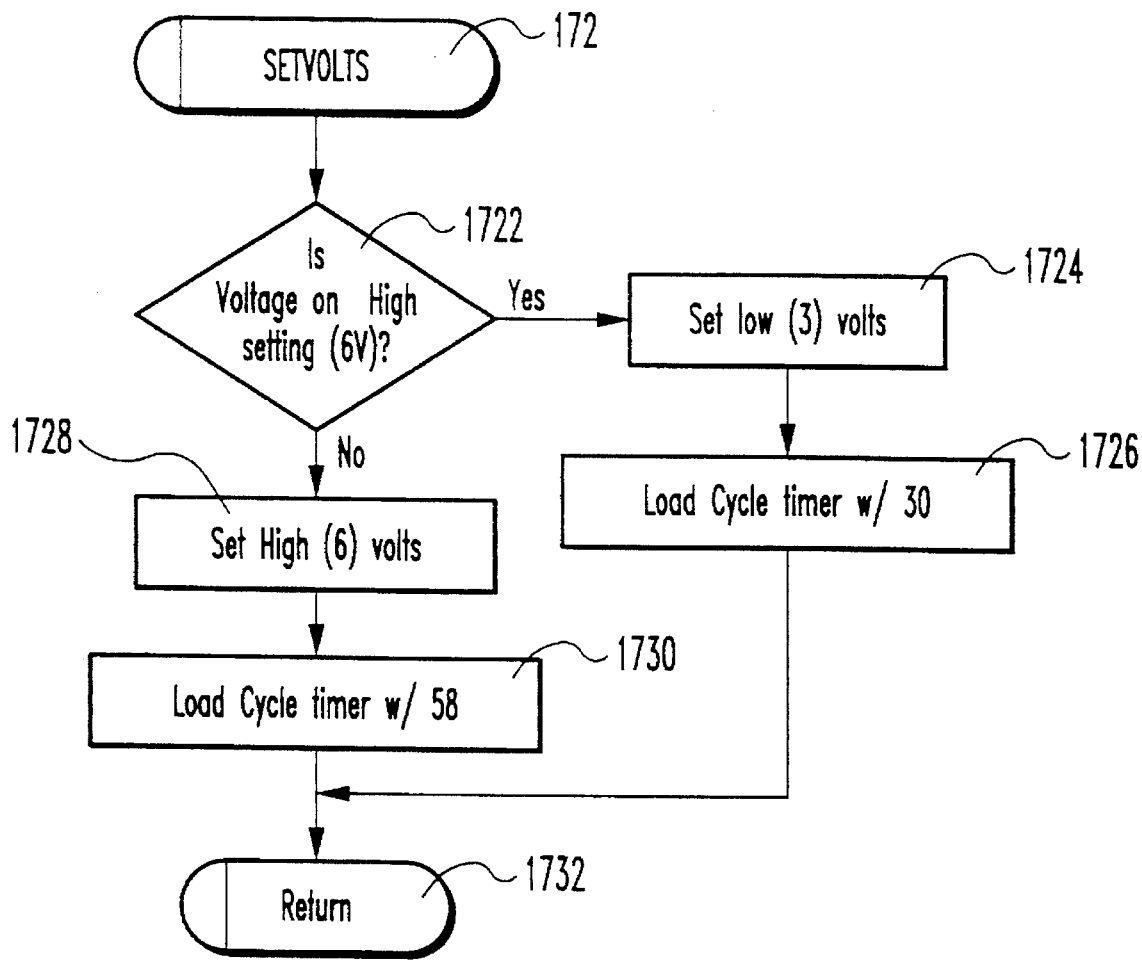
Figures 4, 6B:
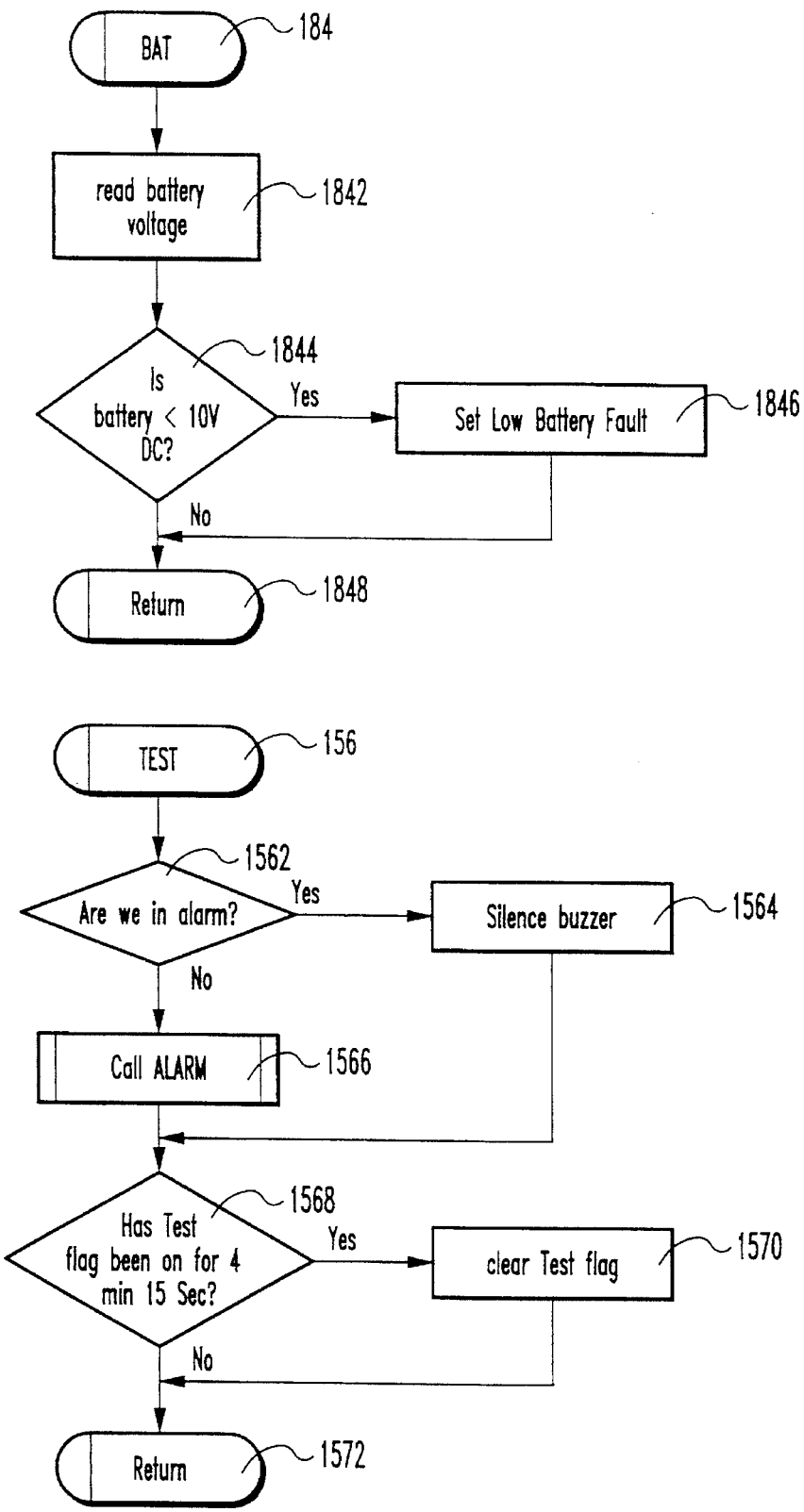
Figure 7A:
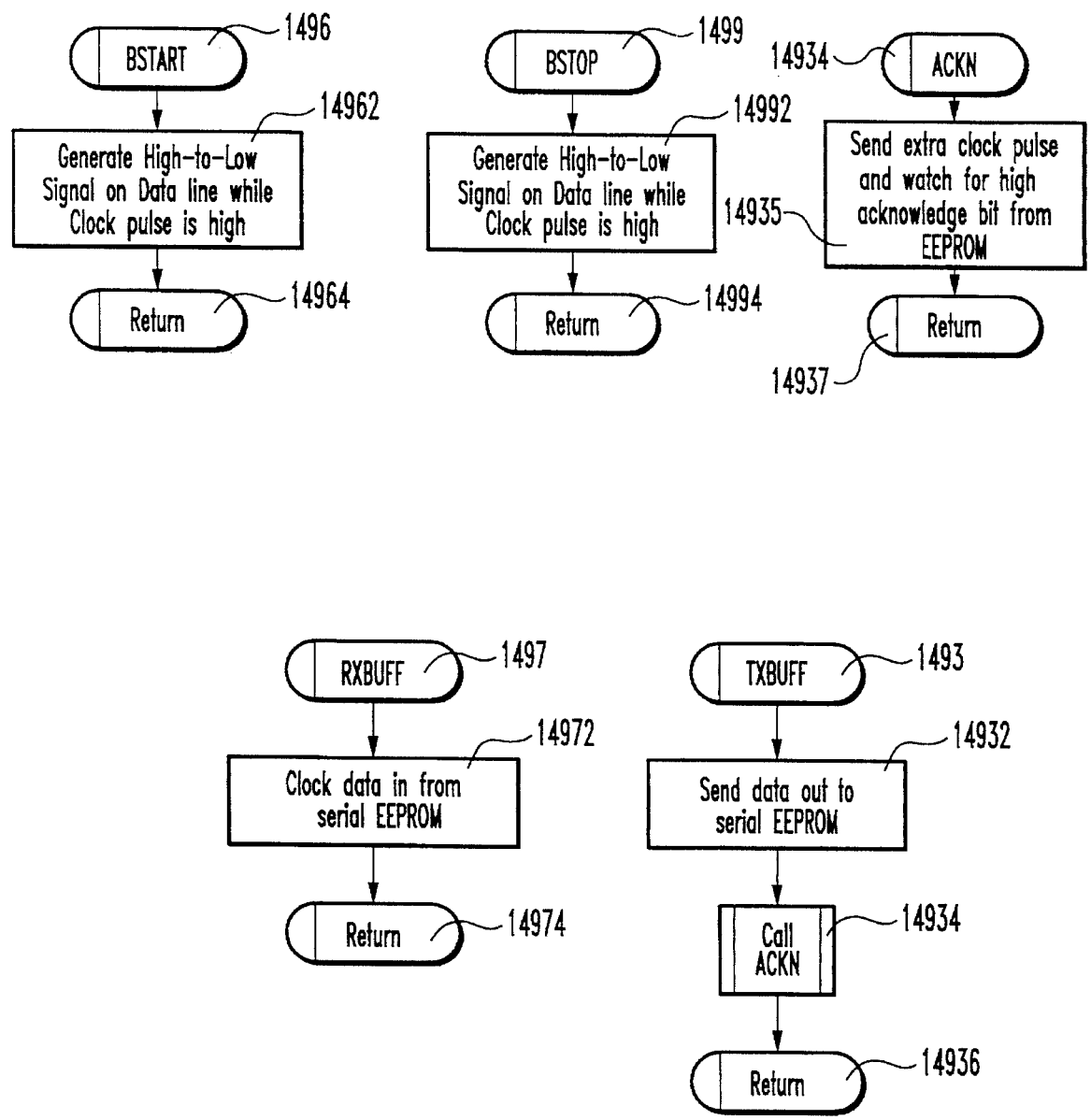
Figures 1, 7B:
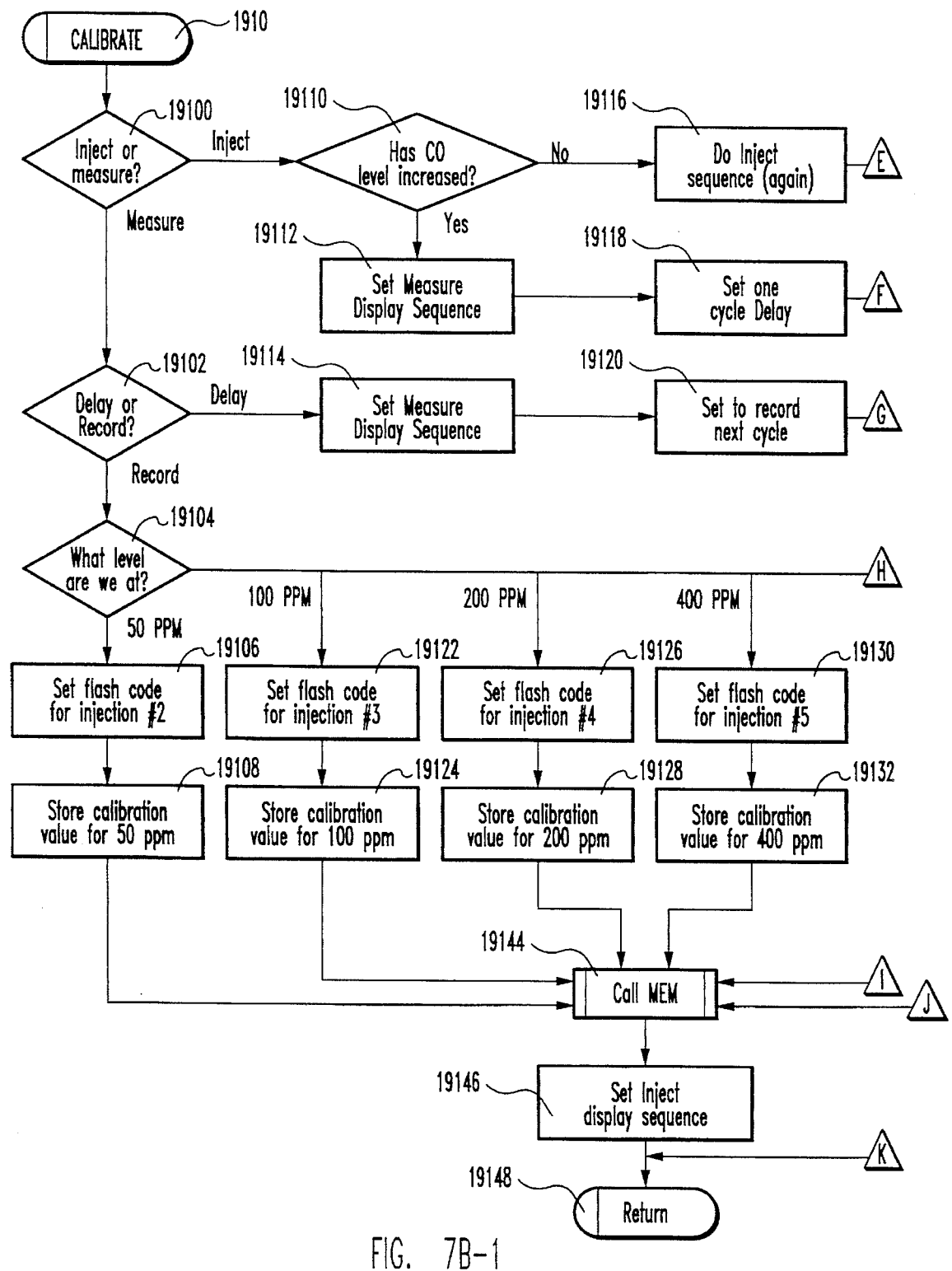
Figures 2, 7B:
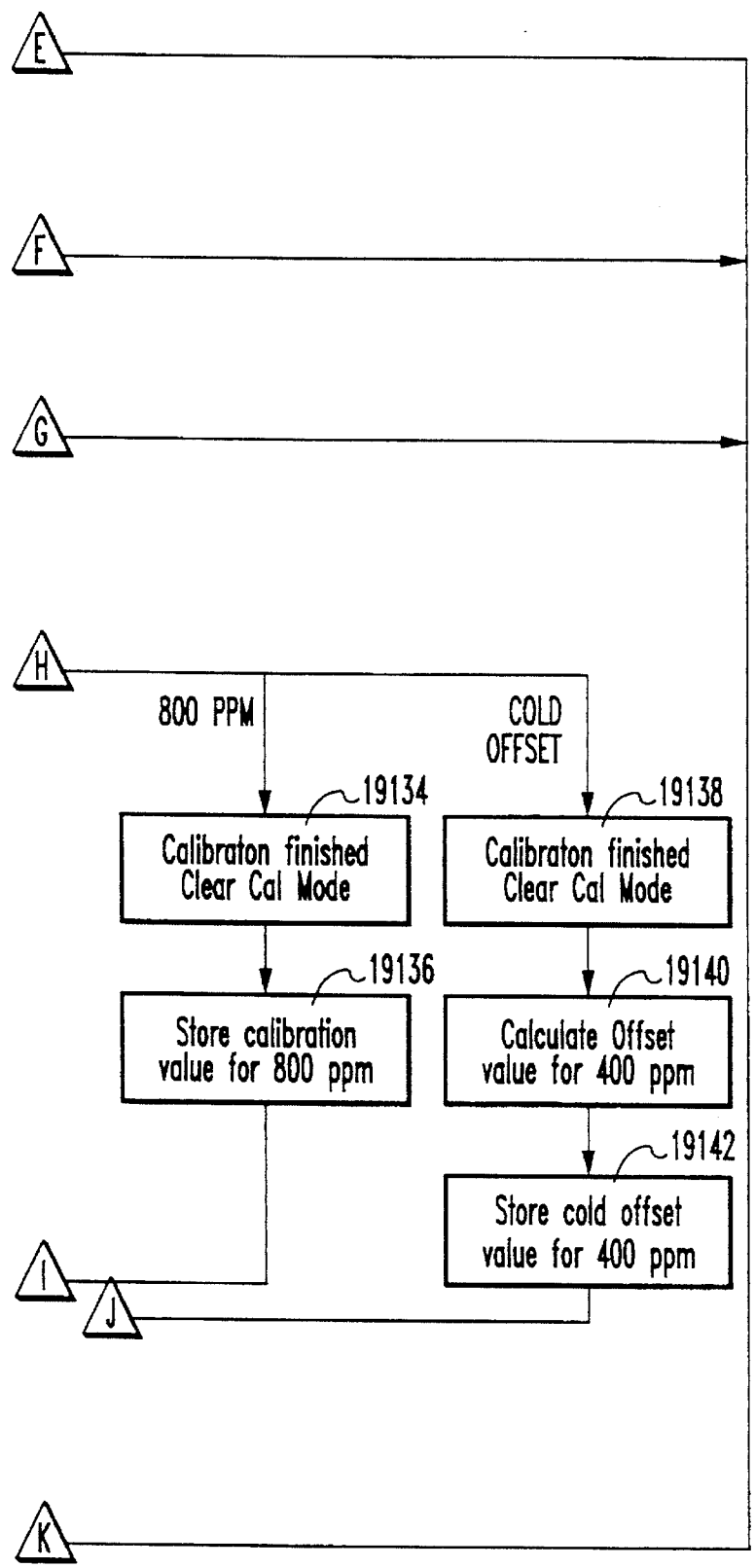
Figure 7C:
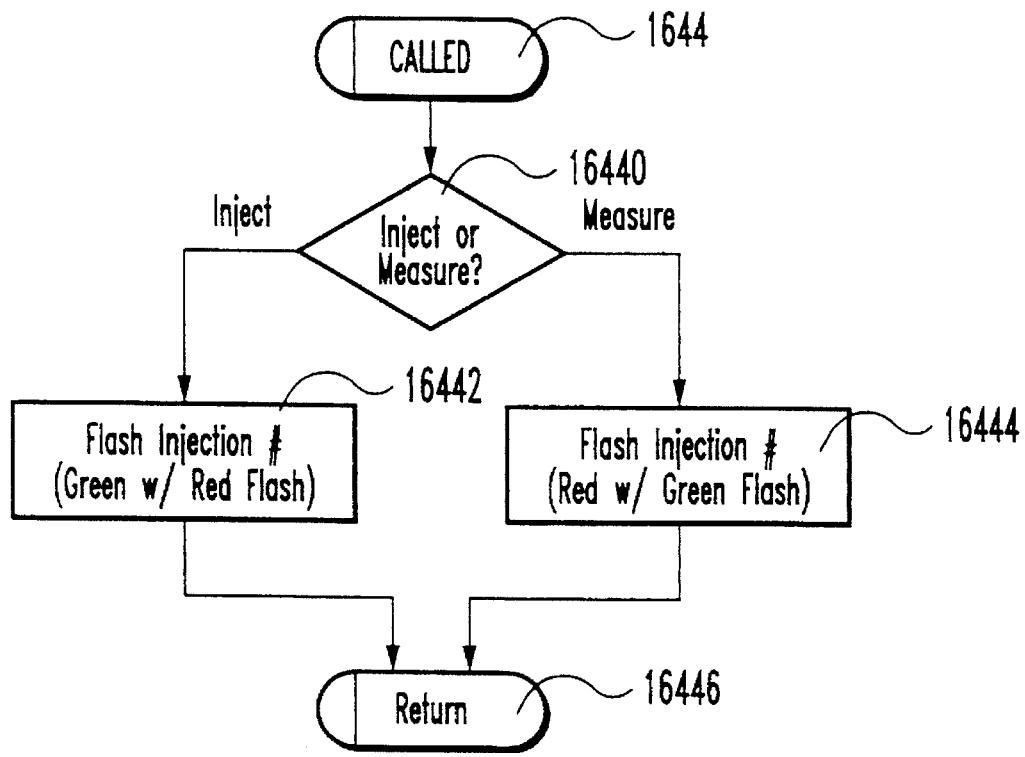
Figure 7C:
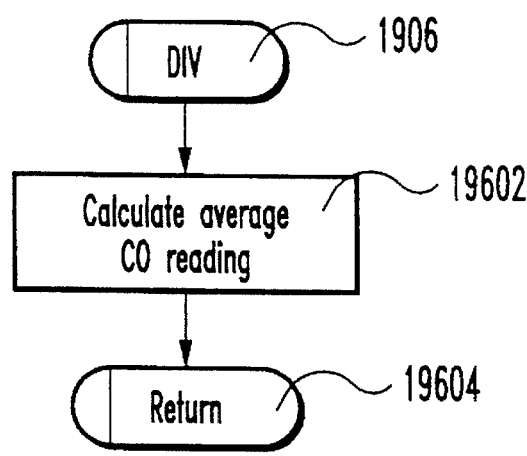

A preferred method for calibrating the gas detection system is shown in steps 1910 through 19148 of FIG. 7B-1 and 7B-2 as the calibration subroutine. During the calibration subroutine the system user removes power from the gas sensor PC board and a shorting plug or jumper is placed across the pins of connector J1 to activate the self calibration or learn mode. The gas detection system is then placed in a sealed chamber at 20°±2° C. at 50–60% relative humidity and power is then applied to the PC board. No LED signal will appear when power is applied to the PC board. This indicates that the system is executing the calibration subroutine and is warming up. The system user and the system follow the procedure as described in the numbered steps below in order to calibrate the gas detection system:

1. When the LED turns green with 1 red flash, a gaseous CO injection is administered to the sealed chamber to establish a level of CO equal to 50 ppm. This condition will continue for 88 seconds.

2. The LED will turn red with 1 green flash for 176 seconds. This is the period of time during which a measurement is taken of the CO concentration level which will be the first calibration level of CO. At the end of this measurement cycle, the microprocessor will progress to the next step.

3. When the LED turns green with 2 red flashes, another injection of CO is made into the sealed container to establish a level of CO equal to 100 ppm. This condition will continue for 88 seconds.

4. The LED will turn red with 2 green flashes for 176 seconds. This is the measurement cycle for the second calibration level of CO. At the end of the cycle, the microprocessor will progress to the next step.

5. When the LED turns green with 3 red flashes, a further CO injection to the container is made to establish a level of CO equal to 200 ppm. This condition will continue for 88 seconds.

6. The LED will turn red with 3 green flashes for 176 seconds. This is the measurement cycle for the third calibration level of CO. At the end of the cycle, the microprocessor will progress to the next step.

7. When the LED turns green with 4 red flashes the system user establishes a level of CO equal to 400 ppm by another CO injection. This condition will continue for 88 seconds.

8. The LED will turn red with 4 green flashes for 176 seconds. This is the measurement cycle for the fourth calibration level of CO. At the end of the cycle, the microprocessor will progress to the next step.

9. When the LED turns green with 5 red flashes the system user establishes a level of CO equal to 800 ppm by a CO injection. This condition will continue for 88 seconds.

10. The LED will turn red with 5 green flashes for 176 seconds. This is the measurement cycle for the fifth and last calibration level of CO. At the end of the cycle, the microprocessor has completed its calibration subroutine.

11. Calibration is complete when the LED turns solid red. Continued exposure to the 800 ppm CO concentration will cause the gas detector to make an audible alarm within 6 minutes.

12. After completion of the calibration cycle, the detector system is placed in a cold chamber and conditioned at a −10° C. with power applied for a minimum of 4 hours. Calibration occurs at −10°±2° C. The shorting plug or jumper is replaced and the gas sensor is reset. No LED signal is displayed until after a subsequent 60 second warmup cycle is complete. The gas detector system then repeats steps 1 and 2, above, with the system user adding 400 ppm of CO via an injection to the sealed container.

13. Following calibration, the shorting plug on J1 is removed and the gas detection system is conditioned for at least 12 more hours, after which the calibration will be validated at 200 ppm of CO.

An expanded flow chart of the gas detection system calibration subroutine, "CALIBRAT", which particularized CO gas concentration measurement to the specific gas sensor and associated electronic circuitry of the system, and beginning at step 1910, is set forth in FIG. 7B-1 and 7B-2. A description of the steps carried out within this subroutine is as follows:

Step 1910:Read the input gas concentration environment from the gas sensor, prompt via the LED for changes to the concentration of CO in the environment, and store the resultant sensor detection of CO concentration data in nonvolatile external RAM memory.

Step 19100:Determine if there is a prompt for an injection, or whether an injection of more CO has been detected by an increase in CO concentration in the environment.

Step 19110:Determine if there is detected an injection by noting if there has been at least a predetermined minimum increase in the sensor input signal.

Step 19116:Where the predetermined minimum increase in CO concentration is not detected by a change in voltage, check for the minimum increase on the next loop through this subroutine.

Step 19112:Set the LED flash sequence to be red and a rapid flash of green on the LED to indicate that the injection of CO to the environment has been detected.

Step 19118:Wait for an 88 second cycle to delay the calibration measurement so as to allow for the gas detection environment to stabilize after an injection of more CO.

Step 19102:Determine if the system is waiting for the gas detection environment to stabilize, or whether the system is ready to record a new gas concentration level.

Step 19114:Set the LED flash sequence to be red and a rapid flash of green on the LED to indicate that the CO injection to the environment has been detected.

Step 19120:Prepare to record the next sensor input signal after approximately 88 seconds.

Step 19104:Determine which level of gas concentration is being calibrated for in order to store a gas concentration level relevant to the level of calibration in external nonvolatile memory.

Step 19106:Prompt the user for the next injection of more CO by displaying on the LED a color pattern of a long green and two red flashes so as to indicate that the concentration level should be raised to 100 ppm.

Step 19108:Prepare RAM contents for communication to EEPROM nonvolatile memory with gas concentration data from a 50 ppm injection into the gas concentration detection environment.

Step 19122:Prompt the user for next injection by displaying green and three red flashes to indicate that the concentration level should be raised to 200 ppm.

Step 19124:Prepare the Ram contents for communication to the external EEPROM nonvolatile memory with data from a gas sensor detection of a concentration of 100 ppm achieved from successive requested injections of CO to the environment.

Step 19126:Prompt the user for the next injection by displaying on the LED a green light and four red flashes to indicate that the concentration level should be raised to 400 ppm.

Step 19128:Prepare RAM contents for communication to EEPROM with data from the 200 ppm injection.

Step 19130:Prompt the user for the next injection by displaying on the LED a green light and five red flashes to indicate that the concentration level of CO should be raised to 800 ppm.

Step 19132:Prepare the RAM contents for communication to the EEPROM with data from the 400 ppm injection.

Step 19134:Inhibit any further execution of the calibration subroutine.

Step 19136:Prepare the RAM contents for communication to the EEPROM with data from 800 ppm injection.

The "COLD OFFSET" branch of the calibration subroutine serves to calculate the gas sensor reading differences between readings at 400 ppm in room temperature and at negative 10 degrees Centigrade.

Step 19138:Inhibit further execution of the calibration subroutine.

Step 19140:Subtract the cold reading at 400 ppm from the room temperature reading at 400 ppm to arrive at the temperature compensation constant as offset data.

Step 19142:Prepare RAM contents for communication to the EEPROM with the temperature compensation offset data. An interpolation calculation will be performed using data from a temperature detecting thermistor and the gas sensor input so as to compensate the gas sensor input signal for cold temperature variations when the sensor is read at temperatures below 5 degrees Centigrade.

Step 19144:Store values in the volatile RAM memory to the nonvolatile memory at specific addresses in the EEPROM data RAM storage area.

Step 19146:Set the flash sequence to be green flash red to indicate the current injection level request to obtain an additional concentration of CO.

Figures 1, 6C:
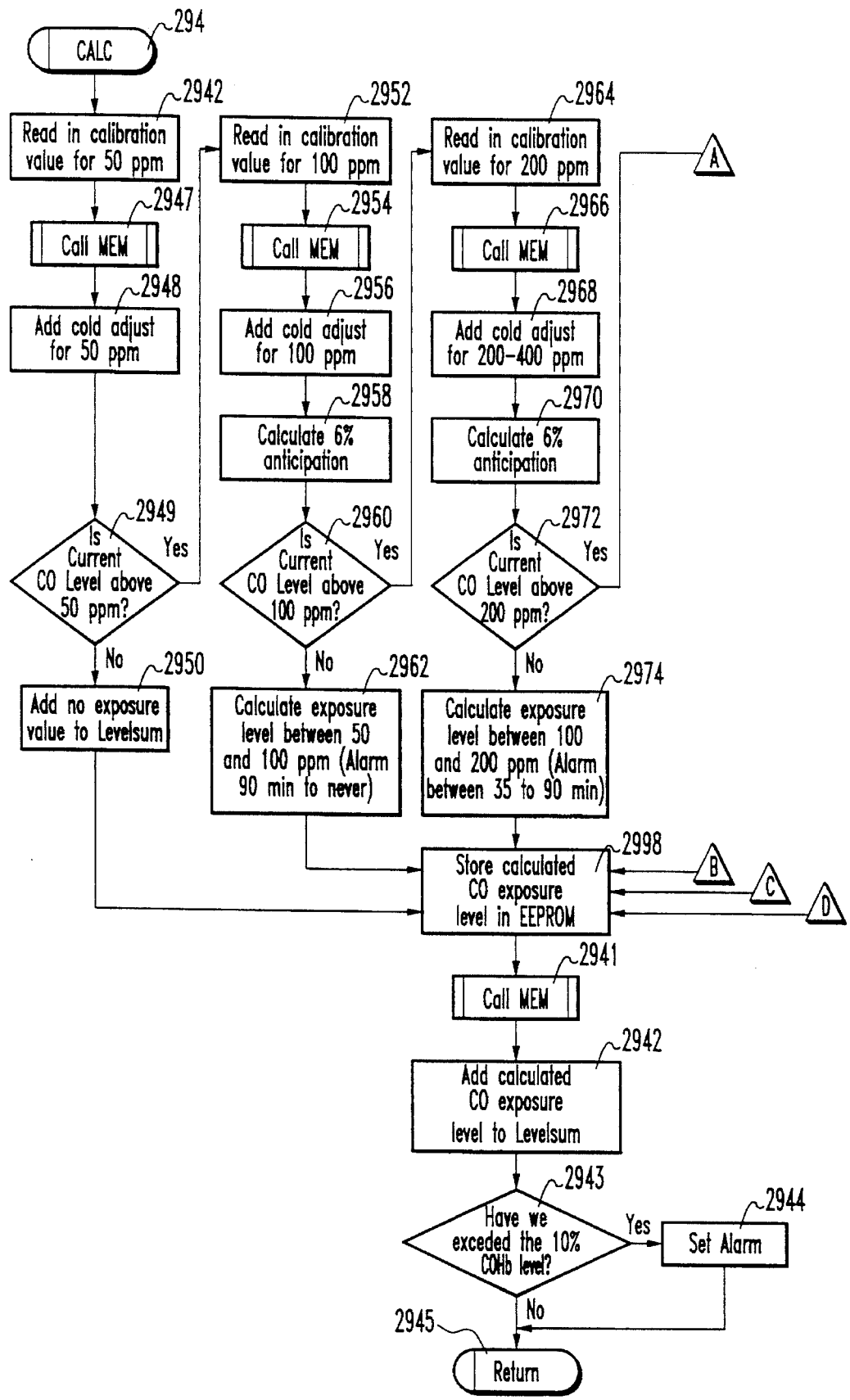
Figures 2, 6C:
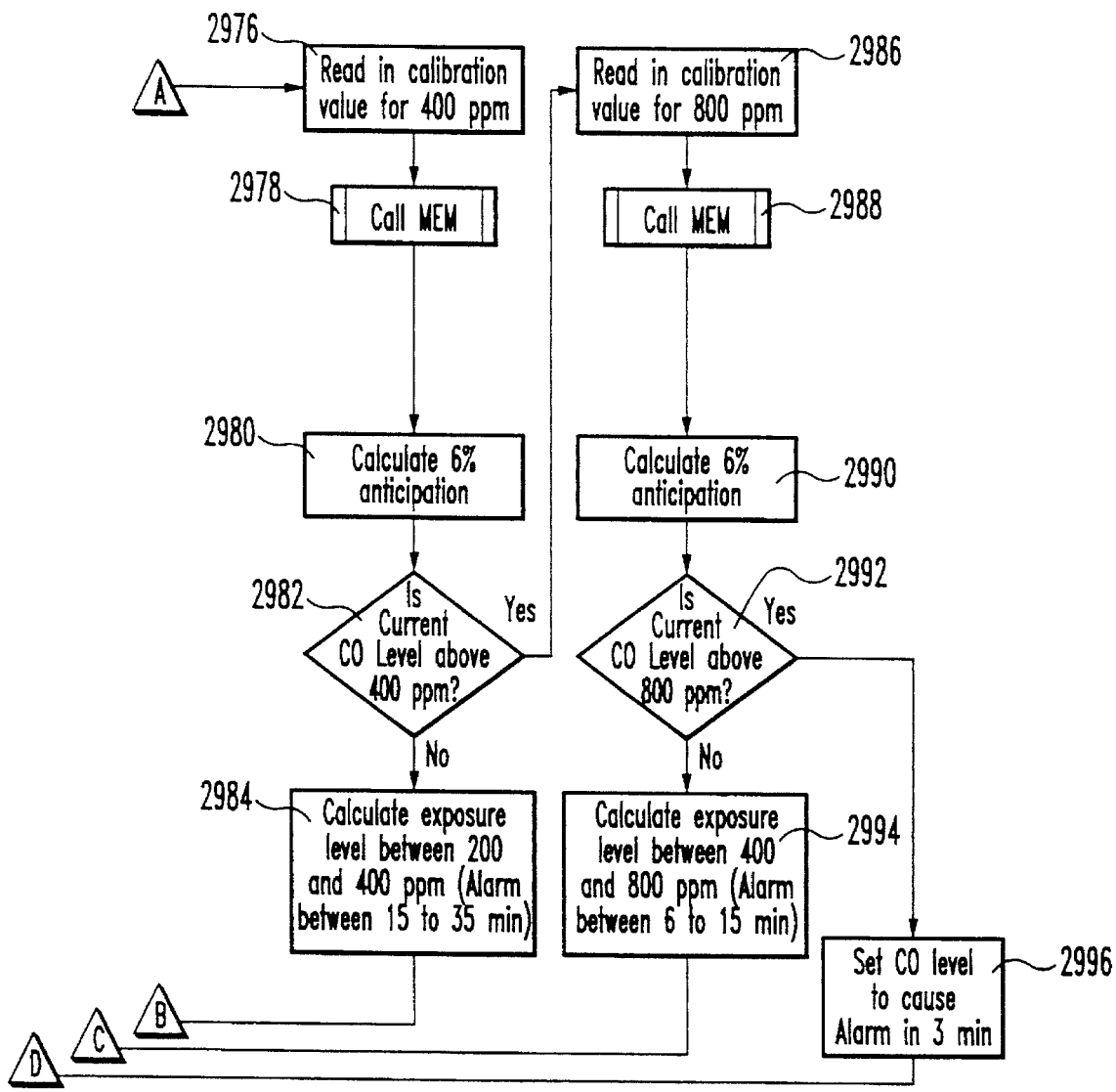
Figure 6D:
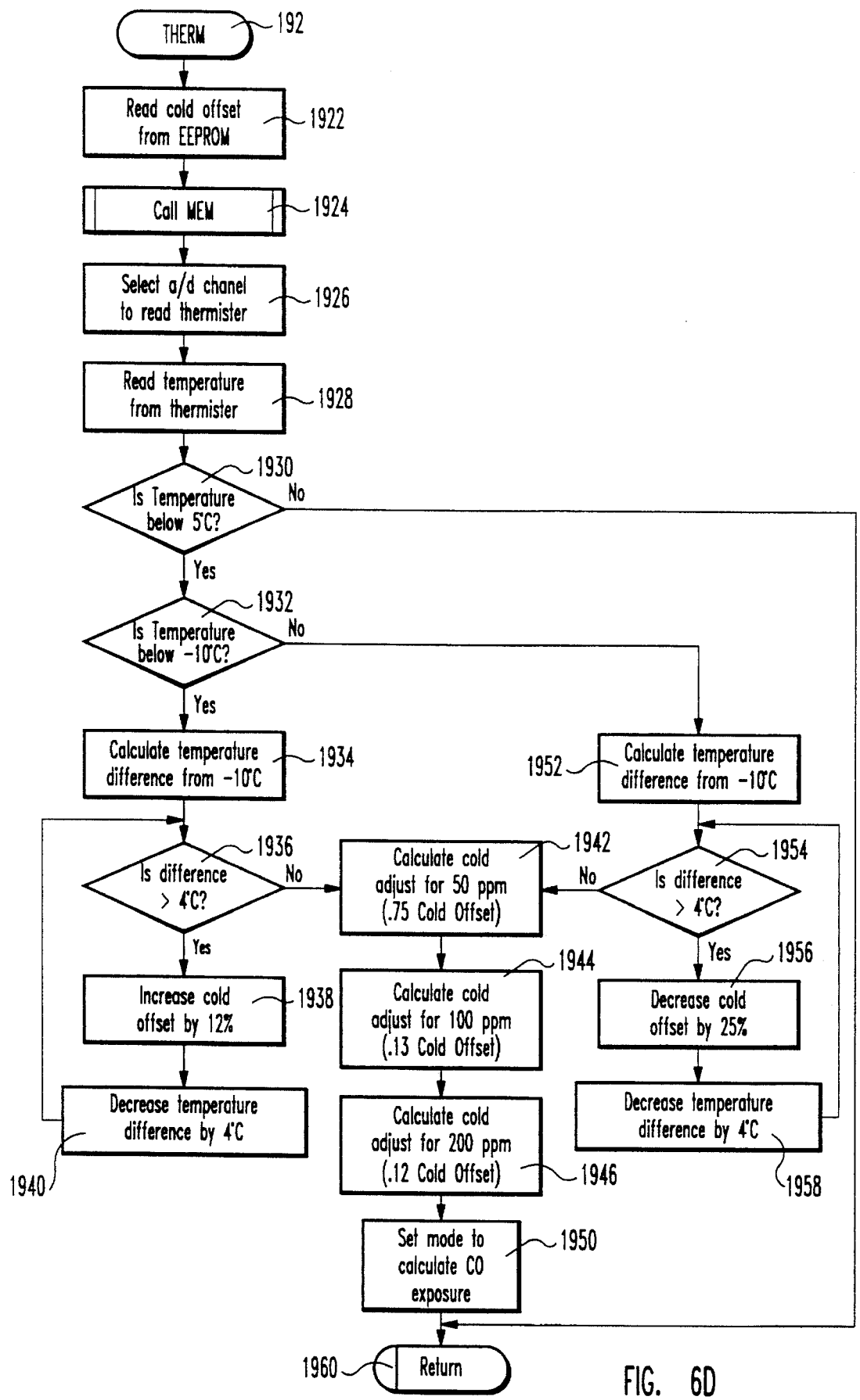
Figure 6E:
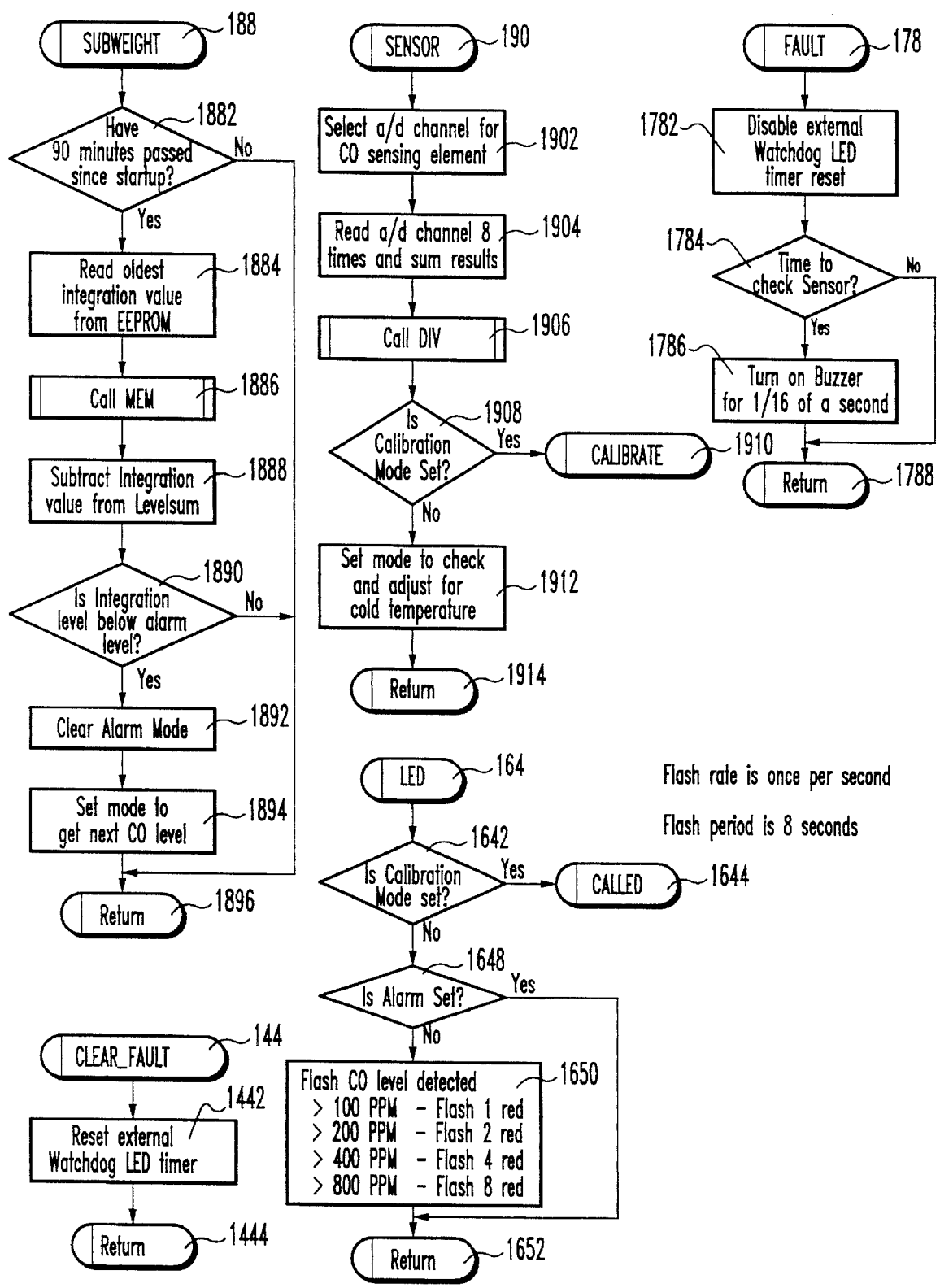

An expanded flow chart of the "CALC" subroutine, which is the CO gas concentration measurement mode, begins at step 294 as set forth in FIG. 6C-1 and 6C-2. A description of the steps carried out within subroutine "CALC: is as follows:

Step 294:Compare the sensor measurement in volatile memory to the stored nonvolatile values obtained during the calibration subroutine.

Step 2942:Recall the calibration data from EEPROM corresponding to the 50 ppm storage register.

Step 2947:Read in the requested data from the nonvolatile memory in the EEPROM.

Step 2948:Add the temperature compensation value to the sensor reading (when the room temperature is above 5 degrees Centigrade, the temperature compensation value that is added will be adjusted to zero).

Step 2949:Determine if the gas sensor value is greater than the 50 ppm value in the EEPROM that was obtained during the calibration subroutine.

Step 2950:Do not make an addition to the calculated total exposure level.

Step 2952:Recall the calibration data from the EEPROM nonvolatile memory corresponding to the 100 ppm storage register which was recorded during the calibration subroutine.

Step 2954:Read in the requested data from the nonvolatile memory in EEPROM.

Step 2956:Add the temperature compensation value to the sensor reading (when the room temperature is above 5 degrees Centigrade, the temperature compensation value that is added will be adjusted to zero).

Step 2958:Subtract a predetermined margin of safety factor from the EEPROM nonvolatile memory data obtained during calibration subroutine for a 100 ppm sensor reading.

Step 2960:Determine if the gas sensor value is greater than the 100 ppm value in the EEPROM obtained during the calibration subroutine as adjusted for an approximate 6% safety margin factor.

Step 2962:Calculate a weighted exposure value according to a predetermined algorithm, which algorithm approximates an actual exposure value as if the gas concentration was constant for a period of ninety minutes. At a constant concentration between 50 ppm and 100 ppm, an alarm condition will not activate according to the present algorithm, and the LED will visibly indicate a CO concentration level below 100 ppm by a steady green color.

Step 2964:Recall the calibration data from EEPROM corresponding to the 200 ppm storage register.

Step 2966:Read in the requested data from the nonvolatile memory in EEPROM.

Step 2968:Add the temperature compensation value to the sensor reading (when the room temperature is above 5 degrees Centigrade, the temperature compensation value that is added will be adjusted to zero).

Step 2970:Subtract a predetermined margin of safety factor from the EEPROM nonvolatile memory data obtained during calibration subroutine for a 200 ppm gas sensor reading.

Step 2972:Determine if the sensor value is greater than the 200 ppm value in the EEPROM obtained during the calibration subroutine as adjusted for an approximate 6% safety margin factor.

Step 2974:Calculate a weighted exposure value, according to a predetermined algorithm, which algorithm approximates an actual exposure value as if the gas concentration was constant for a period of approximately 35 to ninety minutes. At a constant concentration between 100 ppm and 200 ppm, an alarm condition will activate between approximately 35 and 90 minutes according to the present algorithm given the sensed concentration of CO, and the LED will visibly indicate a green color with one red flash every 8 seconds for CO concentrations below 200 ppm.

Step 2976:Recall the calibration data from EEPROM corresponding to the 400 ppm storage register.

Step 2978:Read in the requested data from the nonvolatile memory in EEPROM.

Step 2980:Subtract a predetermined margin of safety factor from the EEPROM nonvolatile memory data obtained during calibration subroutine for a 400 ppm sensor reading. No compensation value is added before this step because the entire compensation value has already been added in the lower level concentration adjustments of the gas sensor reading.

Step 2982:Determine if the detected gas sensor value is greater than the 400 ppm value in the EEPROM obtained during the calibration subroutine as adjusted for an approximate 6% safety margin factor.

Step 2984:Calculate a weighted exposure value according to a predetermined algorithm, which algorithm approximates an actual exposure value as if the gas concentration was constant for a period of approximately 15 to 35 minutes. At a constant concentration between 200 ppm and 400 ppm, an alarm condition will activate between approximately 15 and 35 minutes according to the present algorithm given the sensed concentration of CO, and the LED will visibly indicate a green color with two red flashes every 8 seconds (red flash for 0.5 seconds, green light for 0.5 seconds, red flash for 0.5 second, and solid green for 6.5 seconds) for CO concentration below 400 ppm.

Step 2986:Recall the calibration data from EEPROM corresponding to the 800 ppm storage register.

Step 2988:Read in the requested data from the nonvolatile memory in EEPROM.

Step 2990:Subtract a predetermined margin of safety factor from the EEPROM nonvolatile memory data obtained during the calibration subroutine for a 800 ppm gas sensor reading. No compensation value is added at this step because the entire compensation value has already been added in the lower level concentration adjustments of the sensor reading.

Step 2992:Determine if the detected gas sensor value is greater than the 800 ppm value in the EEPROM obtained during the calibration subroutine as adjusted for an approximate 6% safety margin factor.

Step 2994:Calculate a weighted exposure value according to a predetermined algorithm, which algorithm approximates an actual exposure value as if the gas concentration was constant for a period of approximately 6 to 15 minutes. At a constant concentration between 400 ppm and 800 ppm, an alarm condition will activate between approximately 6 and 15 minutes according to the present algorithm given the sensed concentration of CO, and the LED will visibly indicate a green color with four red flashes every 8 seconds (red flash for 0.5 seconds, green flash for 0.5 seconds, red flash for 0.5 seconds, green flash for 0.5 seconds, red flash for 0.5 second, green flash for 0.5 seconds, red flash for 0.5 seconds, and green flash for 4.5 seconds) to indicate a CO concentration below 800 ppm.

Step 2996:Set a predetermined exposure value to approximate an actual exposure value as if the gas concentration was constant for a period of approximately 3 minutes. At a such a constant concentration, an alarm condition will activate at 3 minutes given the set exposure value, and the LED will visibly indicate a continuous 0.5 red, 0.5 green color pattern cycle.

Step 2998:Set address pointer of nonvolatile RAM memory so that the weighted exposure value will be stored at the oldest address out of the 60 weighted exposure values in nonvolatile RAM memory during the memory storage routine in step 2941.

Step 2941:Store the weighted exposure value where the address pointer is set in step 2998.

Step 2942:Add the weighted exposure value to the accumulated exposure value, which accumulated exposure value is the sum of all sixty weighted exposure values contained in the nonvolatile RAM memory.

Step 2943:Check to see if the accumulated exposure value is at the predetermined alarm level.

Step 2944:Set an alarm condition to activate, which condition is an audible alarm and a predetermined visual CO concentration indicator at the LED, which will be the LED color pattern of a cyclical flashing at 0.25 seconds of red and followed by 0.25 seconds of no illumination.

Step 2945: Return to the calling step.

Subroutines without descriptions above may be understood by referencing their calling routines which are described above, or by the general descriptions for the system and method of the present invention set forth in the brief summary of the invention.

It will be appreciated that the digital processor IC1 of FIG. 2B, which is an 16C71 microprocessor as identified in Table I, could be programmed so as to implement the above-described method using any one of a variety of different programming languages and programming techniques.

The method of the present invention is carried out under the control of a program resident in the 16C71 microcomputer. Those skilled in the art, using the information given herein, will readily be able to assemble the necessary hardware, either by purchasing it off-the-shelf or by fabricating it and properly programming the microprocessor in either a low level or a high level programming language. While it is desirable to utilize clock rates that are as high as possible, and as many bits as possible in the incorporated A/D converters, the application of the embodiment and economic considerations will allow one skilled in the art to choose appropriate hardware for interfacing the microprocessor with the remainder of the embodiment. Also, it should be understood that for reasons of simplifying the diagrams, power supply connections, as well as other necessary structures, are not explicitly shown in the figures, but are provided in actuality using conventional techniques and apparatus.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

TABLE I

| CKT ID | DESCRIPTION | IDENTITY |
|---|---|---|
| C1 | Capacitor, Electrolytic, 10 uF 50 V | 10 uF 50 V |
| C2 | Capacitor, Electrolytic, 1 uF 50 V | 1 uF 50 V |
| C3 | Capacitor, Electrolytic, 1000 uF 25 V | 1000 uF/25 V |
| C4 | Capacitor, Electrolytic, 1000 uF 16 V | 1000 uF/16 V |
| C6 | Capacitor, Ceramic, 1 uF 50 V | 0.1 uF |
| C7 | Capacitor, Ceramic, 1 uF 50 V | 0.1 uF |
| C8 | Capacitor, Ceramic, 1 uF 50 V | 0.1 uF |
| C9 | Capacitor, Ceramic, 1 uF 50 V | 0.1 uF |
| CR1 | Resonator, Ceramic, 4 Mhz | Pan 4000A/ KBR4 00MKS |
| D1 | Diode, Rectifier | 1N4002 |
| D2 | Diode, Rectifier, Fast | 11DQ05 |
| D3 | Diode, Rectifier | 1N4002 |
| IC1 | Microprocessor (50K Pricing) | PIC16C71 |
| IC2 | MEMORY, EEPROM, 128B, SERIAL | 24LC01 |
| J1 | JUMPER, 2 PIN | |
| L1 | INDUCTOR 55 uH | 4632 |
| LED2 | LED, TRISTATE, RECT. RED/GRN | VRBG5641 |
| PCB1 | PCB, Detector (Local Vendor) | Version 1.1 |
| Q1 | Transistor, Power Darlington, PNP | TIP117 |
| Q3 | Transistor, Darlington, PNP | MPSA63 |
| Q4 | Transistor, Darlington PNP | MPSA63 |
| R1 | RESISTOR, 10 MOHM, ¼ W 5% | Equiv to MIL-R-11 |

TABLE I-continued

| CKT ID | DESCRIPTION | IDENTITY |
|---|---|---|
| R10 | RESISTOR, 39 KOHM, ¼ W 5% | Eqiv. to MIL-R-11 |
| R11 | RESISTOR, 10 KOHM, ¼ W 5% | Equiv to MIL-R-11 |
| R13 | RESISTOR, 100 KOHM, ¼ W 5% | Equiv to MIL-R-11 |
| R15 | RESISTOR, 820 KOHM, ¼ W 5% | Equiv to MIL-R-11 |
| R4 | RESISTOR, 1 kohm, ¼ W 5% | Equiv to MIL-R-11 |
| R5 | RESISTOR, 470 OHM, ¼ W 5% | Equiv to MIL-R-11 |
| R6 | RESISTOR, 620, OHM, ¼ W 5% | Equiv to MIL-R-11 |
| R7 | RESISTOR, 220 OHM, ¼ W 5% | Equiv to MIL-R-11 |
| R9 | RESISTOR, XXX KOHM, ¼ W 2% | Identity matched to SEN1 (e.g. 30K, 60K or 90K) |
| REG1 | Regulator 5 V | LM7805 |
| S1 | BUZZER, 24 VDC, 106 DB, OSC | OBO35C2 |
| SEN1 | Sensor, Gas Detection | TGS822 |
| SIP2 | RESISTOR, SIP, 10K, 2%, DISCRETE | Equiv to MIL-R-83401 |
| SW1 | Button, Momentary, Normal Open | B3F1050 |
| TR1 | Transistor, NPN | 2N4401 |
| U1 | Comparator Dual | LM 393 |
| RT1 | Thermister 1K, 5%, ISO-CHIP, Type 1( | 135-102DAG |
| R17 | RESISTOR, 4.64 KOHM, 2% | Equiv to MIL-R-10509 |
| R16 | RESISTOR, 2.4 KOHM, ¼ W 5% | Equiv to MIL-R-11 |
| D7 | Diode, Zener, 3.3 V | IN5226 |
| Q5 | Transistor PNP | 2N4403 |
| R21 | RESISTOR, 5 KOHM, ¼ W, 5% | Equiv to MIL-R-11 |
| SIP3 | RESISTOR, SIP, 10K, 2%, DISCRETE | Equiv to MIL-R-83401 |
| | Wire 18 Gage, Red, UL | AWM-1335 |
| | Wire 18 Gage, Black, UL | AWM-1335 |

What is claimed and desired to be secured by United States Patent is:

1. A system for monitoring a concentration of gaseous carbon monoxide and for automatically recording and displaying gaseous carbon monoxide concentration data, said system comprising:

means for sensing the concentration of the gaseous carbon monoxide and for outputting an electrical signal proportional to the concentration of the gaseous carbon monoxide, the sensing means being placed in fluid communication with the gaseous carbon monoxide, said sensing means comprising:

a catalyzing element and a means for cyclically heating said catalyzing element, said gaseous carbon monoxide catalyzing when in fluid communication with the catalyzing element that is heated to a predetermined catalyzing temperature range, wherein the cyclical heating means heats said catalyzing element by application of a first predetermined electrical voltage for a first predetermined time so as to cause the catalyzing element to be heated above the predetermined catalyzing temperature range, and wherein the cyclical heating means heats said catalyzing element by application of a second predetermined electrical voltage for a second predetermined time so as to cause the catalyzing element to be heated within the predetermined catalyzing temperature range, the sensing means outputting an electrical signal proportional to the concentration of the gaseous carbon monoxide when the catalyzing element is heated within the predetermined catalyzing temperature range;

means for converting said signal output from said sensing means into a series of corresponding digital signals;

data memory means for storing a concentrations history array, said concentrations history array having stored therein for chronological order from an oldest previously stored concentration level of the gaseous carbon monoxide to a newest concentration level of the gaseous carbon monoxide a plurality greater than two of previously stored levels of concentration of the gaseous carbon monoxide, for storing a total exposure level, and for storing a calibration table of values, each value in the calibration table of values corresponding to a predetermined response of the sensing means to being placed in fluid communication with a predetermined concentration of gaseous carbon monoxide;

digital processor means for processing said digital signals so as to electronically monitor, display and record the concentration of the gaseous carbon monoxide by performing a plurality of programmed steps comprising:

comparing the digital signals with said values of the calibration table of values;

deriving data from said comparison step representing a derived gas level that corresponds to the predetermined response of the sensing means to being placed in fluid communication with the corresponding predetermined concentration of gaseous carbon monoxide;

electronically storing the derived gas level in the concentrations history array, said concentrations history array having stored therein a plurality greater than two of previously stored levels of concentration of the gaseous carbon monoxide, each of said previously stored levels of concentration of the gaseous carbon monoxide being stored therein in chronological order from an oldest previously stored concentration level of the gaseous carbon monoxide to at least two chronologically more recent concentration levels of the gaseous carbon monoxide, said derived gas level being stored in said concentrations history array so as to replace the oldest previously stored concentration level of gaseous carbon monoxide;

summing said plurality greater than two of previously stored levels of concentration of the gaseous carbon monoxide to arrive at the total exposure level;

electronically storing the total exposure level in the data memory means;

automatically displaying the derived gas level in a visually perceptible manner to a system user; and automatically displaying in a visually perceptible manner to the system user a diagnostic when the total exposure level exceeds a predetermined alarm level;

program memory means for storing machine-readable instructions utilized by said digital processor means to carry out said plurality of programmed steps; and display means, electrically connected to said digital processor means, for outputting a visual display of the derived gas level, and for outputting a visual display of the diagnostic when the total exposure level exceeds the predetermined alarm level.

2. The system as defined in claim 1, wherein the display means is a single LED that radiates light in a predetermined patterned sequence corresponding to the derived gas level, and that radiates light in a predetermined patterned sequence corresponding to the diagnostic.

3. The system as defined in claim 2, wherein the single LED is a multi-color LED, and wherein the predetermined patterned sequences corresponding to the derived gas level and the diagnostic are both patterned sequences of a plurality of colors of radiated light.

4. The system as defined in claim 1, further comprising a means for producing a sound, and wherein the sound producing means produces an audible alarm when the total exposure level in the data memory means exceeds the predetermined alarm level.

5. The system as defined in claim 1, further comprises a means for measuring an ambient temperature, and wherein the data memory means has stored therein a temperature compensation table of temperature compensation values, each temperature compensation value in the temperature compensation table of temperature compensation values corresponding to a predetermined response of the sensing means to a predetermined range of temperatures, and wherein the programmed step of said plurality of programmed steps of deriving data from said comparison step representing a derived gas level further comprises the steps of:

obtaining an ambient temperature from the ambient temperature measuring means, and adjusting the derived gas level by a temperature compensation value in said temperature compensation table of temperature compensation values corresponding to the ambient temperature obtained from the ambient temperature measuring means.

6. The system as defined in claim 1, wherein the predetermined alarm level corresponds to a predetermined gas concentration exposure over a predetermined time that would cause a predetermined carboxyhemoglobin condition of a theoretical human.

7. The system as defined in claim 1, wherein the cyclical heating means heats said catalyzing element above said predetermined catalyzing temperature range so as to remove a deposit of impurities therefrom.

8. The system as defined in claim 7, wherein the cyclical heating means repeatedly heats said catalyzing element within and above said predetermined catalyzing temperature range, whereby repeatedly the derived gas level is obtained and the catalyzing element has removed therefrom said deposit of impurities.

9. The system as defined in claim 1, wherein the second predetermined voltage is approximately one half of the first predetermined voltage, and the first predetermined time is not greater than twice the second predetermined time.

10. The system as defined in claim 9, wherein the second predetermined voltage is approximately 3 volts, and the second predetermined time is 30 seconds.

11. The system as defined in claim 1, wherein the catalyzing element is surrounded, at least in part, by an active charcoal filter.

12. The system as defined in claim 1, further comprising means, activateable by the system user, for simulating the predetermined alarm level when the total exposure level in the data memory means is not greater than the predetermined alarm level, and wherein the concentrations history array in the data memory means is not changed, whereby the display means outputs a visual display of the diagnostic.

13. A system for monitoring a concentration of a gas and for automatically recording and displaying gas concentration data, said system comprising:

means for sensing the concentration of the gas and for outputting an electrical signal proportional to the concentration of the gas, the sensing means being placed in fluid communication with the gas;

means for converting said signal output from said sensing means into a series of corresponding digital signals;

data memory means for storing a concentrations history array, said concentrations history array having stored therein in chronological order from an oldest previously stored concentration level of the gas to a newest concentration level of the gas a plurality greater than two of previously stored levels of concentration of the gas, for storing a total exposure level, and for storing a calibration table of values, each said value in the calibration table corresponding to a predetermined response of the sensing means to being placed in fluid communication with a predetermined concentration of gas;

digital processor means for processing said digital signals so as to electronically monitor, display and record the concentration of the gas by performing a plurality of programmed steps comprising:

comparing the digital signals with values of the calibration table;

deriving data from said comparison step representing a derived gas level that corresponds to the predetermined response of the sensing means to being placed in fluid communication with the corresponding predetermined concentration of gas;

electronically storing the derived gas level in the concentrations history array, said concentrations history array having stored therein a plurality greater than two of previously stored levels of concentration of the gas, each of said previously stored levels of concentration of the gas being stored therein in chronological order from an oldest previously stored concentration level of the gas to at least two chronologically more recent concentration levels of the gas, said derived gas level being stored in said concentrations history array so as to replace the oldest previously stored concentration level of gas in the data memory means;

summing said plurality greater than two of previously stored levels of concentration of the gas to arrive at the total exposure level;

electronically storing the total exposure level in the data memory means;

automatically displaying the derived gas level in a visually perceptible manner to a system user; and automatically displaying in a visually perceptible manner to the system user a diagnostic when the total exposure level in the data memory means exceeds a predetermined alarm level;

program memory means for storing machine-readable instructions utilized by said digital processor means to carry out said plurality of programmed steps; and display means, electrically connected to said digital processor means, for outputting a visual display of the derived gas level, and for outputting a visual display of the diagnostic when the total exposure level exceeds the predetermined alarm level.

14. The system as defined in claim 13, wherein the display means is a single LED that radiates light in a predetermined patterned sequence corresponding to the derived gas level, and that radiates light in a predetermined patterned sequence corresponding to the diagnostic.

15. The system as defined in claim 14, wherein the single LED is a multi-color LED, and wherein the predetermined patterned sequences corresponding to the derived gas level and the diagnostic are both patterned sequences of a plurality of colors of radiated light.

16. The system as defined in claim 13, further comprising a means for producing a sound, and wherein the sound producing means produces an audible alarm when the total exposure level in the data memory means exceeds the predetermined alarm level.

17. The system as defined in claim 13, further comprises a means for measuring an ambient temperature, and wherein the data memory means has stored therein a temperature compensation table of temperature compensation values, each temperature compensation value in the temperature compensation table of temperature compensation values corresponding to a predetermined response of the sensing means to a predetermined range of temperatures, and wherein the programmed step of said plurality of programmed steps of deriving data from said comparison step representing a derived gas level further comprises the steps of:

obtaining an ambient temperature from the ambient temperature measuring means, and adjusting the derived gas level by a temperature compensation value in said of temperature compensation table of temperature compensation values corresponding to the ambient temperature obtained from the ambient temperature measuring means.

18. The system as defined in claim 13, wherein the predetermined alarm level corresponds to a predetermined gas concentration exposure over a predetermined time that would cause a predetermined blood gas concentration of the gas in a hemoglobin content in a vascular blood supply of a theoretical human.

19. The system as defined in claim 13, wherein said sensing means further comprises a catalyzing element and a means for cyclically heating said catalyzing element, said gas catalyzing when in fluid communication with the catalyzing element that is heated to a predetermined catalyzing temperature range, the sensing means outputting an electrical signal proportional to the concentration of the gas when the catalyzing element is heated within the predetermined catalyzing temperature range.

20. The system as defined in claim 19, wherein the cyclical heating means heats said catalyzing element above said predetermined catalyzing temperature range so as to remove a deposit of impurities therefrom.

21. The system as defined in claim 20, wherein the cyclical heating means repeatedly heats said catalyzing element within and above said predetermined catalyzing temperature range, whereby repeatedly the derived gas level is obtained and the catalyzing element has removed therefrom said deposit of impurities.

22. The system as defined in claim 19, wherein the cyclical heating means heats said catalyzing element by application of a first predetermined electrical voltage for a first predetermined time so as to cause the catalyzing element to be heated above the predetermined catalyzing temperature range, and wherein the cyclical heating means heats said catalyzing element by application of a second predetermined electrical voltage for a second predetermined time so as to cause the catalyzing element to be heated within the predetermined catalyzing temperature range.

23. The system as defined in claim 22, wherein the gas is essentially composed of carbon monoxide.

24. The system as defined in claim 23, wherein the catalyzing element is surrounded, at least in part, by an active charcoal filter.

25. The system as defined in claim 22, wherein the second predetermined voltage is approximately one half of the first predetermined voltage, and the first predetermined time is not greater than twice the second predetermined time.

26. The system as defined in claim 25, wherein the second predetermined voltage is approximately 3 volts, and the second predetermined time is 30 seconds.

27. The system as de lined in claim 13, further comprising means, activateable by the system user, for simulating the predetermined alarm level when the total exposure level in the data memory means is not greater than the predetermined alarm level, and wherein the concentrations history array in the data memory means is not changed, whereby the display means outputs a visual display of the diagnostic.

28. A system for monitoring a concentration of a gas and for automatically recording and displaying concentration data, comprising:

means for sensing the concentration of the gas and for outputting an electrical signal proportional to the concentration of the gas, the sensing means being placed in fluid communication with the gas;

means for converting said signal output from said sensing means into a series of corresponding digital signals;

digital processor means for processing said digital signals so as to electronically monitor, display and record the concentration of the gas by performing a plurality of programmed steps comprising:

deriving data from said digital signals which represents a level of concentration of the gas;

electronically storing the level of concentration of the gas as a newest concentration level of the gas in a concentrations history array, said concentrations history array having stored therein in chronological order from an oldest previously stored concentration level of the gas to the newest concentration level of the gas a plurality greater than two of previously stored levels of concentration of the gas;

subtracting the oldest previously stored concentration level of the gas from a sum of the plurality of previously stored concentration levels of the gas to arrive at an intermediate sum;

adding the level of the concentration of the gas to the intermediate sum to arrive at a total exposure level;

electronically storing the total exposure level for later retrieval and output;

automatically displaying the level of concentration of the gas in a visually perceptible manner to a system user; and automatically displaying in a visually perceptible manner to the system user a diagnostic when the total exposure level exceeds a predetermined alarm level;

data memory means for storing the total exposure level and the concentrations history array;

program memory means for storing machine-readable instructions utilized by said digital processor means to carry out said plurality of programmed steps; and display means, electrically connected to said digital processor means, for outputting a visual display of the level of concentration of the gas and a visual display of the diagnostic when the total exposure level exceeds the predetermined alarm level.

29. A system for monitoring a concentration of a gas and for automatically recording and displaying gas concentration data, said system comprising:

means for sensing the concentration of the gas, said sensing means comprising:

a catalyzing element;

a heating material separate from and in thermal communication with said catalyzing element;

a means for cyclically heating said heating material, said cyclical heating means heating said catalyzing element by application of a first predetermined electrical voltage for a first predetermined time to said heating material so as to cause the catalyzing element to be heated above a catalyzing temperature range of the gas, and wherein the cyclical heating means heats said heating material by application of a second predetermined electrical voltage for a second predetermined time so as to cause the catalyzing element to be heated within the catalyzing temperature range of the gas;

a means for continuous sensing of the catalyzing element, wherein said continuous sensing means senses said catalyzing element when the catalyzing element is heated both above and within the catalyzing temperature range of the gas, and for continuously outputting an electrical signal proportional to the concentration of the gas in fluid communication with the catalyzing element when the catalyzing element is heated to a temperature within the catalyzing temperature range of the gas;

means for converting said electrical signal output from said means for continuous sensing of the catalyzing element into a series of corresponding digital signals;

digital processor means for processing said digital signals so as to electronically monitor, display and record the concentration of the gas in fluid communication with the catalyzing element by performing a plurality of programmed steps comprising:

deriving data from said digital signals which represents a level of concentration of the gas; and automatically displaying the level of concentration of the gas in a visually perceptible manner to a system user;

program memory means for storing machine-readable instructions utilized by said digital processor means to carry out said plurality of programmed steps; and display means, electrically connected to said digital processor means, for outputting a visual display of the level of the concentration of the gas.

30. The system as defined in claim 29, wherein an electrical voltage is continuously applied to the heating material by the cyclical heating means; and wherein said cyclical heating means and said continuous sensing means are separate electrically isolated electrical circuits.

31. The system as defined in claim 29, wherein the first predetermined time and the continuous second predetermined time are a cycle having a duration of less than 90 seconds, and wherein the catalyzing element catalyzes all of the gas in fluid communication therewith during the first predetermined time, and wherein the temperature of the catalyzing element drops below the catalyzing temperature range of the gas during the second predetermined time.

32. The system as defined in claim 29, further comprising:

data memory means for storing a concentrations history array, said concentrations history array having stored therein in chronological order from an oldest previously stored concentration level of the gas to a newest concentration level of the gas a plurality greater than two of previously stored levels of concentration of the gas, for storing a total exposure level, and for storing a calibration table of values, each said value in the calibration table of values corresponding to a predetermined response of the sensing means to being placed in fluid communication with a predetermined concentration of the gas;

wherein the plurality of programed steps performed by the digital processor means further comprises:

comparing the digital signals with said values of the calibration table of values;

deriving data from said comparison step representing a derived gas level that corresponds to the predetermined response of the sensing means to being placed in fluid communication with the corresponding predetermined concentration of the gas, wherein said level of concentration of the gas is the derived gas level;

electronically storing the derived gas level in the concentrations history array, said concentrations history array having stored therein a plurality greater than two of previously stored levels of concentration of the gas, each of said previously stored levels of concentration of the gas being stored therein in chronological order from an oldest previously stored concentration level of the gas to at least two chronologically more recent concentration levels of the gas, said derived gas level being stored in said concentrations history array so as to replace the oldest previously stored concentration level of the gas;

summing said plurality greater than two of previously stored levels of concentration of the gas to arrive at the total exposure level;

electronically storing the total exposure level in the data memory means; and automatically displaying in a visually perceptible manner to the system user a diagnostic when the total exposure level exceeds a predetermined alarm level; and wherein said display means is also for outputting a visual display of the diagnostic when the total exposure level exceeds the predetermined alarm level.

33. The system as defined in claim 29, wherein the gas is gaseous carbon monoxide.

* * * * *